United States Patent
Olf et al.

(10) Patent No.: US 12,071,516 B2
(45) Date of Patent: *Aug. 27, 2024

(54) POLYMERIC STABILIZING FORMULATIONS

(71) Applicant: Nano Precision Medical, Inc., Emeryville, CA (US)

(72) Inventors: Ryan Olf, Emeryville, CA (US); Lyle Gordon, Emeryville, CA (US); Wouter Roorda, Emeryville, CA (US)

(73) Assignee: Nano Precision Medical, Inc., Alameda, CA (US)

( * ) Notice: Subject to any disclaimer, the term of this patent is extended or adjusted under 35 U.S.C. 154(b) by 706 days.

This patent is subject to a terminal disclaimer.

(21) Appl. No.: 17/241,818

(22) Filed: Apr. 27, 2021

(65) Prior Publication Data

US 2021/0246271 A1    Aug. 12, 2021

Related U.S. Application Data

(63) Continuation-in-part of application No. PCT/US2021/019559, filed on Feb. 25, 2021, and a continuation-in-part of application No. 16/600,249, filed on Oct. 11, 2019, now Pat. No. 11,021,576, which is a continuation of application No. 15/508,572, filed as application No. PCT/US2015/048677 on Sep. 4, 2015, now Pat. No. 10,479,868.

(60) Provisional application No. 62/983,296, filed on Feb. 28, 2020, provisional application No. 62/045,834, filed on Sep. 4, 2014.

(51) Int. Cl.

| A61K 31/7088 | (2006.01) |
|---|---|
| A61K 9/00 | (2006.01) |
| A61K 31/541 | (2006.01) |
| A61K 38/26 | (2006.01) |
| A61K 47/60 | (2017.01) |
| C08G 83/00 | (2006.01) |
| A61K 38/02 | (2006.01) |
| A61K 38/20 | (2006.01) |
| A61K 38/22 | (2006.01) |

(52) U.S. Cl.
CPC .......... *C08G 83/003* (2013.01); *A61K 9/0024* (2013.01); *A61K 31/541* (2013.01); *A61K 38/26* (2013.01); *A61K 47/60* (2017.08); *A61K 38/02* (2013.01); *A61K 38/208* (2013.01); *A61K 38/22* (2013.01)

(58) Field of Classification Search
None
See application file for complete search history.

(56) References Cited

U.S. PATENT DOCUMENTS

| 4,694,064 | A | 9/1987 | Tomalia et al. |
|---|---|---|---|
| 4,694,084 | A | 9/1987 | Breuninger et al. |
| 6,190,650 | B1 | 2/2001 | Matthews et al. |
| 6,902,744 | B1 | 6/2005 | Kolterman et al. |
| 7,955,614 | B2 | 6/2011 | Martin et al. |
| 9,511,212 | B2 | 12/2016 | Roorda |
| 9,770,412 | B2 | 9/2017 | Mendelsohn et al. |
| 9,814,867 | B2 | 11/2017 | Mendelsohn et al. |
| 10,045,943 | B2 | 8/2018 | Roorda |
| 10,479,868 | B2 * | 11/2019 | Mendelsohn ........ A61K 9/0024 |
| 11,021,576 | B2 * | 6/2021 | Mendelsohn .......... A61K 38/26 |
| 2005/0147581 | A1 | 7/2005 | Zamiri et al. |
| 2008/0260840 | A1 | 10/2008 | Alessi et al. |
| 2010/0036000 | A1 | 2/2010 | Lichter et al. |
| 2011/0311621 | A1 | 12/2011 | Salama et al. |
| 2012/0029062 | A1 | 2/2012 | Gunaratne et al. |

FOREIGN PATENT DOCUMENTS

| CN | 107929718 | 4/2018 | |
|---|---|---|---|
| WO | 2013022801 | 2/2013 | |
| WO | 2013085951 | 6/2013 | |
| WO | WO-2013085951 A1 * | 6/2013 | .......... A61K 38/212 |
| WO | 2016037128 | 3/2016 | |

OTHER PUBLICATIONS

International Application No. PCT/US2015/048677, International Preliminary Report on Patentability mailed on Mar. 16, 2017, 10 pages.
International Application No. PCT/US2015/048677, International Search Report and Written Opinion mailed on Jan. 19, 2016, 12 pages.
International Application No. PCT/US2021/019559, International Search Report and Written Opinion mailed on Jun. 11, 2021, 13 pages.

* cited by examiner

*Primary Examiner* — Brian Gulledge
(74) *Attorney, Agent, or Firm* — Kilpatrick Townsend & Stockton LLP

(57) ABSTRACT

The disclosure pertains to the field of treatment of patients with implantable delivery devices for long-term release of therapeutic agents. In particular, the disclosure provides devices and methods for the stabilization of the therapeutic agents inside the device for the duration of the implantation. The devices control the long-term release of the therapeutic agents by using a nanoporous membrane. The stabilization is achieved by using high-molecular weight stabilizers of a size that is larger than the diameter of the pores of the membrane, thereby preventing the release of the stabilizers.

20 Claims, 7 Drawing Sheets

POLYMERIC STABILIZING FORMULATIONS

CROSS-REFERENCES TO RELATED APPLICATIONS

The present application is a continuation-in-part of U.S. application Ser. No. 16/600,249, allowed, filed Oct. 11, 2019, which application is a continuation of U.S. patent application Ser. No. 15/508,572, filed Mar. 3, 2017, now U.S. Pat. No. 10,479,868, which application is a 371 national stage application of International Application No. PCT/US2015/048677, filed Sep. 4, 2015, which application claims priority to U.S. Provisional Application No. 62/045,834, filed Sep. 4, 2014.

The present application is also a continuation-in-part of PCT/US2021/019559, filed Feb. 25, 2021, which application claims priority to U.S. Patent Application No. 62/983,296, filed Feb. 28, 2020, the disclosures all of which are hereby incorporated by reference in their entireties for all purposes.

BACKGROUND

Many subjects, human as well as veterinary, are in need of long-term treatment with therapeutic agents. In order to improve adherence, many subjects would benefit from the compliance provided by an implantable device releasing a desired therapeutic agent at a desired rate and at a desired purity for an extended period of time. Since many therapeutic agents have limited stability under conditions of implantation, long-term stabilization of the therapeutic agents may be required.

WO 2008/061355 is drawn to an implantable hydrogel device for administration of GLP-1 or an analogue of GLP-1 for sustained release over extended periods of time as well as methods of manufacture.

WO 2009/158412 is drawn to implantable devices, formulations and methods of making implantable device for the release of a polypeptide from the implantable device. This reference uses a hydrogel for sustained release of the polypeptide.

In view of the above, there is a need for devices and formulations for long term release and stabilization of therapeutic agents, for methods of stabilization of the therapeutic agents, and for methods of preparation and use of such devices and formulations. The present disclosure satisfies these and other needs.

BRIEF SUMMARY

In one embodiment, the present disclosure provides a method for stabilizing a pharmaceutical composition in a capsule configured to be implanted, the method comprising:
  providing a pharmaceutical composition comprising a therapeutic agent, which therapeutic agent is a peptide, together with a polymeric stabilizing agent comprising a polymer having a plurality of stabilizing groups, wherein the polymer is a dendritic polymer or is a cross-linked polymer;
  providing a capsule having a reservoir and a nanoporous membrane with a plurality of pores, wherein said pharmaceutical composition is disposed within the reservoir, the capsule configured for implantation; and
  the polymeric stabilizing agent having molecular dimensions larger than the pore size of the nanoporous membrane, wherein the release of the polymeric stabilizing agent from the reservoir is substantially prevented; and wherein the nanoporous membrane is a diffusion pathway out of the reservoir for the therapeutic agent.

In some instances, the therapeutic agent is selected from the group consisting of beta-glucocerobrosidase, interferon alpha, interferon beta, agasidase alpha, agasidase beta, exenatide, nutropin/somatropin, factor VIII, fondaparinux, aldesleukinand, risperidone, forigerimod, NP fusion proteins, IL-12, a melanocyte stimulating hormone, and bapineuzumab.

In some instances, the therapeutic agent is selected from the group consisting of exenatide, octreotide and fluphenazine.

In some instances, the therapeutic agent comprises exenatide.

In some instances, the polymer is a dendritic polymer.

In some instances, the polymer is a poly(amidoamine) dendrimer having a plurality of end groups, wherein the plurality of end groups comprise at least one member selected from the group consisting of the acid groups, the base groups, alkyl, hydroxyalkyl, amidoethanol, amidoethylethanolamine, ethylenediamine, sodium carboxylate, succinamic acid, trimethoxysilyl, tris(hydroxymethyl) amidomethane, and 3-carbomethoxypyrrolidinone.

In some instances, the end groups of the poly(amidoamine) dendrimer comprise sodium carboxylate.

In some instances, each stabilizing group is independently selected from the group consisting of an acid group, a base group, an anti-oxidant, an anti-microbial, an anti-biotic, a protein clustering agent, and a protein declustering agent.

In some instances, each stabilizing group is independently selected from the group consisting of an acid group and a base group.

In some instances, the acid groups are selected from the group consisting of carboxylic acid, amino acid, thiol, and phenol.

In some instances, the acid groups are carboxylic acids.

In some instances, the base groups are selected from the group consisting of hydroxy, cyano, amine and carboxylate.

In some instances, the base groups are amines.

In some instances, the polymer has a molecular diameter of at least 3 nm.

In some instances, the polymer has a molecular diameter of at least 5 nm.

In some instances, the polymer is an acidic polymer selected from the group consisting of polyacrylic acid, polymethacrylic acid, polystyrene sulfonic acid, polyvinyl sulfonic acid, polyvinyl phosphonic acid and polystyrene phosphonic acid.

In some instances, the polymer is crossed-linked.

In some instances, the polymer is polyacrylic acid.

In some instances, the polymer is polymethacrylic acid.

In some instances, the implantable drug delivery device contains a second membrane.

In some instances, an embodiment of the disclosure includes a device for sustained release of a therapeutic agent, the device comprising:
  a capsule configured for implantation and having a reservoir;
  a nanoporous membrane with a plurality of pores;
  the therapeutic agent disposed within the reservoir; and
  a polymeric stabilizing agent, disposed within the reservoir and comprising an insoluble polymer having a plurality of pH sensitive stabilizing groups;
  wherein the nanoporous membrane provides a diffusion path for the therapeutic agent out of the reservoir; and wherein the polymeric stabilizing agent has dimensions larger than the pore size of the nanoporous membrane substantially preventing release of the polymeric stabilizing agent from the reservoir.

In some instances, the insoluble polymer is a cross-linked polymer.

In some instances, the therapeutic agent is a peptide or protein.

In some instances, the therapeutic agent is an incretin mimetic.

In some instances, the therapeutic agent is exenatide.

In some instances, the therapeutic agent and the stabilizing agent are present in a substantially dry solid form.

In some instances, the device further comprising a solvent for the therapeutic agent.

In some instances, the stabilizing agent includes one or both of acrylic acid residues and methacrylic residues.

In some instances, the pH sensitive stabilizing groups are neutralized to an extent that upon hydration of the therapeutic agent and the stabilizing agent with an aqueous medium having a neutral pH a fluid develops with a pH between about 3.5 and about 7.5.

In some instances, a fluid develops with a pH between about 5.0 and about 6.0.

In some instances, the stabilizing groups are neutralized between about 10% and about 75%, such as about 10%, 12%, 14%, 16%, 18%, 20%, 22%, 24%, 26%, 28%, 30%, 32%, 34%, 36%, 38%, 40%, 42%, 44%, 46%, 48%, 50%, 52%, 54%, 56%, 58%, 60%, 62%, 64%, 66%, 68%, 70%, 72%, 74%, and/or 75%.

In some instances, the stabilizing groups are neutralized between about 30% and about 65%.

In some instances, the solvent has a pH between about 3.5 and about 7.5.

In some instances, the solvent has a pH between about 5.0 and about 6.0.

In some instances, an embodiment of the disclosure includes a method for stabilizing a therapeutic agent, the method comprising:
  providing a device for sustained release of the therapeutic agent, the device comprising:
  a capsule configured for implantation and having a reservoir;
  a nanoporous membrane with a plurality of pores;
  disposing the therapeutic agent within the reservoir; and
  disposing a polymeric stabilizing agent within the reservoir, the polymeric stabilizing agent comprising an insoluble polymer having a plurality of pH sensitive stabilizing groups;
  wherein the nanoporous membrane provides a diffusion path for the therapeutic agent out of the reservoir; and
  wherein the polymeric stabilizing agent has dimensions larger than the pore size of the nanoporous membrane substantially preventing release of the polymeric stabilizing agent from the reservoir.

In some instances, the insoluble polymer is a cross-linked polymer.

In some instances, the therapeutic agent is a peptide or protein.

In some instances, the therapeutic agent is an incretin mimetic.

In some instances, the therapeutic agent is exenatide.

In some instances, the therapeutic agent and the stabilizing agent are present in a substantially dry solid form.

In some instances, the device further comprising a solvent for the therapeutic agent.

In some instances, the stabilizing agent includes one or both of acrylic acid residues and methacrylic residues.

In some instances, the pH sensitive stabilizing groups are neutralized to an extent that upon hydration of the therapeutic agent and the stabilizing agent with an aqueous medium having a neutral pH a fluid develops with a pH between about 3.5 and about 7.5.

In some instances, a fluid develops with a pH between about 5.0 and about 6.0.

In some instances, the stabilizing groups are neutralized between about 10% and about 75%.

In some instances, the stabilizing groups are neutralized between about 30% and about 65%.

In some instances, the solvent has a pH between about 3.5 and about 7.5.

In some instances, the solvent has a pH between about 5.0 and about 6.0.

In some instances, an embodiment of the disclosure includes a method of treating a disease in a subject in need thereof, the method comprising:
  administering to the subject a therapeutically effective amount of a pharmaceutical composition of claim 1 comprising a therapeutic agent and a polymer functionalized with a plurality of stabilizing, thereby treating the disease.

In some instances, an embodiment of the disclosure includes a therapeutic formulation, the formulation comprising:
  a therapeutic agent; and
  a polymeric stabilizing agent comprising an insoluble polymer having a plurality of pH sensitive stabilizing groups, which is a member selected from the group consisting of a cross-linked poly-acrylic acid, a cross-linked poly-methacrylic acid, or mixtures thereof or copolymers of acrylic and methacrylic acid.

In some instances, the pH sensitive stabilizing groups are neutralized to an extent that upon hydration of the therapeutic agent and the stabilizing agent with an aqueous medium having a neutral pH a fluid develops with a pH between about 3.5 and about 7.5.

In some instances, the insoluble polymer is a cross-linked polymer.

In some instances, the therapeutic agent is a peptide or protein.

In some instances, the therapeutic agent is an incretin mimetic.

In some instances, the therapeutic agent is exenatide.

In some instances, the therapeutic agent and the stabilizing agent are present in a substantially dry solid form.

In some instances, the formulation further comprises a solvent for the therapeutic agent.

In some instances, the stabilizing agent includes one or both of acrylic acid residues and methacrylic residues.

In some instances, the pH sensitive stabilizing groups are neutralized to an extent that upon hydration of the therapeutic agent and the stabilizing agent with an aqueous medium having a neutral pH a fluid develops with a pH between about 4.0 and about 7.0

In some instances, a fluid develops with a pH between about 5.0 and about 6.0.

In some instances, the stabilizing groups are neutralized between about 10% and about 75%.

In some instances, the stabilizing groups are neutralized between 30% and 65%.

In some instances, the solvent has a pH between about 3.5 and about 7.5.

In some instances, the solvent has a pH between about 5.0 and about 6.0.

In some instances, the present disclosure provides an implantable drug delivery system, said implantable drug delivery system comprising:
a capsule suitable for implantation;
a reservoir encapsulated by the capsule;
a membrane in contact with the reservoir, wherein the reservoir contains a pharmaceutical composition of a therapeutic agent, which therapeutic agent is a peptide, together with a polymeric stabilizing agent comprising a polymer having a plurality of stabilizing groups, wherein the polymer is a dendritic polymer or is a cross-linked polymer;
said capsule having a nanoporous membrane with a plurality of pores;
said plurality of stabilizing groups having molecular dimensions larger than the pore size of the nanoporous membrane; and wherein the release of said polymeric stabilizing agent from the reservoir is substantially prevented.

In some instances, the therapeutic agent is selected from the group consisting of beta-glucocerobrosidase, interferon alpha, interferon beta, agasidase alpha, agasidase beta, exenatide, nutropin/somatropin, factor VIII, fondaparinux, aldesleukinand, risperidone, forigerimod, NP fusion proteins, IL-12, a melanocyte stimulating hormone, and bapineuzumab.

In some instances, the therapeutic agent is selected from the group consisting of exenatide, octreotide and fluphenazine.

In some instances, the therapeutic agent comprises exenatide.

In some instances, the polymer is a dendritic polymer.

In some instances, the polymer is a poly(amidoamine) dendrimer having a plurality of end groups, wherein the plurality of end groups comprise at least one member selected from the group consisting of the acid groups, the base groups, alkyl, hydroxyalkyl, amidoethanol, amidoethylethanolamine, ethylenediamine, sodium carboxylate, succinamic acid, trimethoxysilyl, tris(hydroxymethyl)amidomethane, and 3-carbomethoxypyrrolidinone.

In some instances, the end groups of the poly(amidoamine) dendrimer comprise sodium carboxylate.

In some instances, each stabilizing group is independently selected from the group consisting of an acid group, a base group, an anti-oxidant, an anti-microbial, an anti-biotic, a protein clustering agent, and a protein declustering agent.

In some instances, each stabilizing group is independently selected from the group consisting of an acid group and a base group.

In some instances, the acid groups are selected from the group consisting of carboxylic acid, amino acid, thiol, and phenol.

In some instances, the base groups are selected from the group consisting of hydroxy, cyano, amine and carboxylate.

In some instances, the polymer is polyacrylic acid.
In some instances, the polymer is polymethacrylic acid.
In some instances, the polymer is co-polymer.
In some instances, the polymer is co-polymer.
In some instances, the implantable drug delivery device contains a second nanoporous membrane.
In some instances, the second membrane provides a diffusion pathway for the therapeutic agent.
In some instances, the pH of the composition is from about 3 to 7.

In some instances, the present disclosure provides an implantable drug delivery system, said implantable drug delivery system comprising:
a capsule having a nanoporous membrane with a plurality of pores, the capsule configured for implantation;
a reservoir encapsulated by the capsule, the reservoir containing a pharmaceutical composition, said pharmaceutical composition comprising:
a therapeutic agent, which therapeutic agent is a peptide, together with a polymeric stabilizing agent comprising a polymer having a plurality of stabilizing groups, wherein the polymer is a dendritic polymer or is a cross-linked polymer;
the polymeric stabilizing agent comprising a polymer having a plurality of stabilizing groups having molecular dimensions larger than the pore size of the nanoporous membrane, wherein the release of the polymeric stabilizing agent from the reservoir is substantially prevented; and wherein the nanoporous membrane is a diffusion pathway out of the reservoir for the therapeutic agent.

In some instances, the therapeutic agent is selected from the group consisting of exenatide, octreotide and fluphenazine.

In some instances, the therapeutic agent comprises exenatide.

In some instances, the polymer is polymethacrylic acid.
In some instances, the polymer is crossed-linked.
In some instances, the polymer is co-polymer.

These and other embodiments, aspects, and objects will become more apparent when read with the drawings which follow.

DETAILED DESCRIPTION

I. General

Figure 1A:
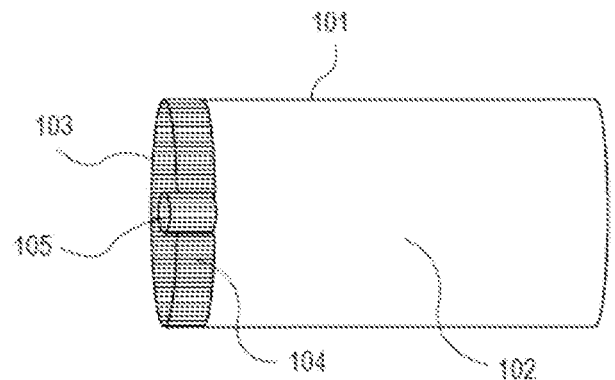
FIG. 1A represents an embodiment of a device with a single reservoir.

The present disclosure provides compositions, specifically polymers, that act as a stabilizing agent in the reservoir of an implantable drug delivery system. The buffered environment in the reservoir of the implantable drug delivery system can help stabilize the therapeutic agent delivered from the device. For example, the polymeric stabilizing agent can be a polymeric buffering agent which can include any number of acid groups or base groups to buffer the composition in the reservoir of the device. The preferred pH of the composition can depend on the therapeutic agent in the reservoir, and be acidic or basic. The present disclosure also includes an implantable drug delivery system incorporating the composition of the present disclosure, as well as methods of treating diabetes using the compositions and implantable drug delivery system of the present disclosure.

The disclosure pertains to the field of long-term treatment of subjects with implantable devices providing a sustained delivery of therapeutic agents.

Embodiments of the disclosure include devices, methods and formulations including one or more therapeutic agents together with one or more polymeric stabilizing agents.

Furthermore, embodiments of the disclosure include methods for the fabrication of the devices.

Additionally, embodiments of the disclosure include methods of treatment of a subject with devices and formulations of the disclosure.

II. Definitions

"Therapeutic agent" refers to any agent capable of providing a therapeutic response, such as a drug or biologic.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

"Membrane" refers to a substrate allowing diffusion of molecules from one side of the membrane to the other through the membrane.

"Titania nanotube membrane" refers to an array of titania nanotubes on a titanium substrate where at least a portion of the titania nanotubes are open at both ends and capable of allowing diffusion of liquids or solids from one side of the membrane to the other through the titania nanotubes.

"Fluid contact" refers to the contents of the reservoir being able to be released or diffuse from the reservoir to the titania nanotubes. The contents of the reservoir can be in liquid form, but can also be in powder or solid form.

"Aspect ratio" refers to the ratio of length to diameter of the titania nanotubes, including the internal and external diameter.

"Zero-order rate of release" refers to the rate of release that is independent of concentration of the therapeutic agent in the reservoir.

"Treat," "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing or retarding the onset of the symptom. The treatment or amelioration of symptoms can be based on any objective or subjective parameter; including, e.g., the result of a physical examination.

"Subject" refers to animals such as mammals, including, but not limited to, primates (e.g., humans), cows, sheep, goats, horses, dogs, cats, rabbits, rats, mice and the like. In certain embodiments, the subject is a human.

"Therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

"Diabetes" or "diabetes mellitus" refers to the group of metabolic diseases having raised blood sugar levels for an extended period of time. Diabetes includes type 1 diabetes, resulting from a lack of insulin production, and type 2 diabetes, which results from insulin resistance where the cells no longer respond to insulin and can progress to a lack of insulin. Other forms of diabetes are known to one of skill in the art.

"Polymeric buffering agent" refers to a polymer having suitable ionizable groups such as acid or base functional groups to buffer a mixture. "Polymer" refers to a macromolecule comprising at least one series of monomer groups. The monomers include, but are not limited to, acrylates, methacrylates, acrylamides, methacrylamides, styrenes, vinyl-pyridine, vinyl-pyrrolidone and vinyl esters such as vinyl acetate. The polymer can adopt a variety of architectures, such as linear, branched, hyperbranched, star, dendritic, cross-linked, comb, etc. The polymer can include a variety of different monomer units in any suitable configuration. For example, linear polymers from at least two different monomers can form block copolymers or random copolymers.

"Acid" refers to a compound that is capable of donating a proton ($H^+$) under the Bronsted-Lowry definition, or is an electron pair acceptor under the Lewis definition. Acids useful in the present disclosure are Bronsted-Lowry acids that include, but are not limited to, alkanoic acids or carboxylic acids (formic acid, acetic acid, citric acid, lactic acid, oxalic acid, etc.), sulfonic acids and mineral acids, as defined herein. Mineral acids are inorganic acids such as hydrogen halides (hydrofluoric acid, hydrochloric acid, hydrobromice acid, etc.), halogen oxoacids (hypochlorous acid, perchloric acid, etc.), as well as sulfuric acid, nitric acid, phosphoric acid, chromic acid and boric acid. Sulfonic acids include methanesulfonic acid, benzenesulfonic acid, p-toluenesulfonic acid, triflouromethanesulfonic acid, among others.

"Base" refers to a compound capable of accepting a proton ($H^+$) under the Bronsted-Lowry definition, or is an electron pair donor under the Lewis definition. Representative bases include, but are not limited to, hydroxy, alkylhydroxy, amines (—NRR), alkylamine, arylamine, amide (—C(O)NRR), sulfonamide (—S(O)$_2$NRR), phosphonamide (—P(O)(—NRR)$_2$), carboxylate (—C(O)O$^-$), and others.

"Molecular diameter" refers to the diameter of the sphere of gyration of a polymer, which is a physical measure of the size of a molecule, and is defined as two times the mass weighted average distance from the core of a molecule to each mass element in the molecule. Stokes diameter or hydrodynamic diameter reflects the dimension of a molecule plus its associated water molecules as it moves through an aqueous solution, and is defined as the radius of an equivalent hard sphere diffusing at the same rate as the molecule under observation.

"Poly(amidoamine) dendrimer" or "PAMAM dendrimer" refers to a dendrimer having amidoamine branching units. Dendrimers also include a single core, and a plurality of surface groups. Dendrimers can be referred to by the "Generation," which describes the number of branching points between the core and the surface groups, where a Generation 1 PAMAM dendrimer has four amido groups linked to an ethylenediamine core. A Generation 2 PAMAM dendrimer has 8 amido groups linked to the 4 amino surface groups of the Generation 1 PAMAM dendrimer. A Generation 3 PAMAM dendrimer then has 16 surface amino groups, a Generation 4 has 32 surface amino groups, and so on. Different cores can result in different numbers of surface groups at each generation. For example, using a core such as trisaminomethyl results in 6 surface amines for Generation 1, then 12 surface amines for Generation 2, 24 surface amines for Generation 3, and so on.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Alkylhydroxy" or "hydroxyalkyl" refers to an alkyl group, as defined above, where at least one of the hydrogen atoms is replaced with a hydroxy group. As for the alkyl group, alkylhydroxy groups can have any suitable number of carbon atoms, such as $C_{1-6}$. Exemplary alkylhydroxy groups include, but are not limited to, hydroxy-methyl, hydroxy-ethyl (where the hydroxy is in the 1- or 2-position), hydroxypropyl (where the hydroxy is in the 1-, 2- or 3-position), hydroxybutyl (where the hydroxy is in the 1-, 2-, 3- or 4-position), hydroxypentyl (where the hydroxy is in the 1-, 2-, 3-, 4- or 5-position), hydroxyhexyl (where the hydroxy is in the 1-, 2-, 3-, 4-, 5- or 6-position), 1,2-dihydroxyethyl, and the like.

"Amidoethanol" refers to the group having the structure "—C(O)NH—CH₂CH₂OH".

"Amidoethylethanol" refers to the group having the structure "—C(O)NH—CH₂CH₂—NH—CH₂CH₂OH".

"Amine" refers to the group having the structure "—NH₂". Other amines include aminoalkyl, where alkyl is defined as above. When the hydrogens are replaced with other groups, the amine can be a secondary amine or tertiary amine. Quaternary amines are those having four groups linked to the nitrogen atom, "—NR₃⁺".

"Ethylendieamine" refers to the group having the structure "—NH—CH₂CH₂—NH—".

"Sodium carboxylate" refers to the group having the structure "—C(O)O⁻Na⁺".

"Succinamic acid" refers to the group having the structure "—C(O)NH—C(O)—CH₂CH₂—C(O)OH".

"Trialkoxysilyl" refers to the group having the structure "—C(O)—CH₂CH₂—C(O)O—CH₂CH₂CH₂—Si(OAlkyl₃)₃". Trialkoxysilyl includes any suitable alkoxy group as described above.

"Tris(hydroxymethyl)amidomethane" refers to the group have the structure "—C(O)NH—C(CH₂OH)₃".

"3-carbomethoxypyrrolidinone" refers to the group having the structure:

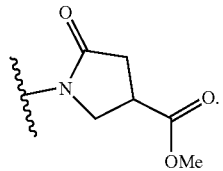 [SMILES: *N1CC(C(=O)OC)CC1=O]

"Consisting of" is a transitional claim term that excludes any element, step or component not specified in the claim.

"Consisting essentially of" is a transitional claim term that limits the scope of a claim to the specified elements, steps or components, and those that do not materially affect the basic and novel characteristic(s) of the claimed invention. "Consisting essentially of" is between the closed claims written in a "consisting of" format and the fully open claims drafted in a "comprising" format.

Incretin mimetics refers to agents that act like incretin hormones such as glucagon-like peptide-1 (GLP-1). They bind to GLP-1 receptors and stimulate glucose dependent insulin release, therefore acting as antihyperglycemics.

Exenatide (natural, recombinant and synthetic, also called exendin-4) refers to amino acid sequence His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser. (CAS Number: 141758-74-9).

"Formulation of a therapeutic agent" refers to the actual state in which a therapeutic agent is present in a product or in a product fabrication intermediate, and includes the therapeutic agent, plus, optionally, any used additional therapeutic agents, any used formulation excipients and any used formulation solvents.

"Porous membranes" refers to membranes characterized by the presence of a two-phase system, in which membrane matrix material represents one phase, typically a continuous phase, which is permeated by open channels extending from one side of the membrane to the other, and filled with a second phase, often a fluid phase, through which mass transport through the membrane can take place.

"Dense" or "non-porous membranes" refers to membranes without fluid filled pores. In such membranes mass transport may take place by a dissolution-diffusion mechanism, in which therapeutic agents permeate the membrane by dissolving in the membrane material itself, and diffusing through it.

"Nanoporous membrane" and "nanopore membrane" are used interchangeably, and refer to porous membranes in which the pores have a smallest diameter of less than 1000 nanometer.

"Nanotube membrane" refers to a nanoporous membrane, wherein pores are formed by an array of nanotubes.

"Stokes diameter" or "hydrodynamic diameter" refers to the dimension of a molecule plus its associated water molecules as it moves through an aqueous solution, and is defined as the radius of an equivalent hard sphere diffusing at the same rate as the molecule under observation.

"Ion exchange resin" refers to a polymer comprising acidic or basic groups, or a combination thereof, made insoluble, for instance by cross-linking, and capable of exchanging anions or cations, or a combination thereof, with a medium surrounding it.

"Fluid" and "fluid form" as used in this disclosure refers to flowable states of matter and includes, but is not limited to gases, solutions, suspensions, emulsions, colloids, dispersions and the like.

"Neutral pH" refers to a pH between 6.5 and 7.5.

III. Device

Figure 1B:
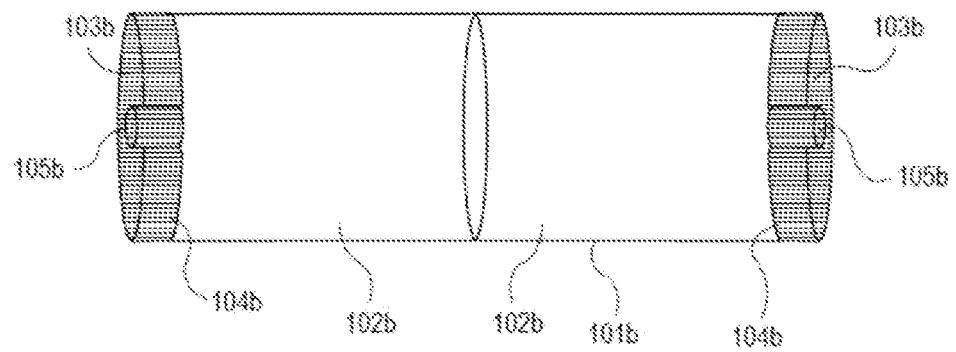
FIG. 1B represents an embodiment of a device with 2 reservoirs.

As illustrated in FIG. 1A, devices of the disclosure include a capsule 101 suitable for implantation, wherein the capsule has a reservoir 102 suitable for holding a therapeutic agent and a stabilizing agent. In some embodiments, more than one reservoir is present. (FIG. 1B). The capsule may be made of any suitable biocompatible material. In some embodiments, the capsule is made of a medical grade metal, such as titanium or stainless steel, or of a medical grade polymeric material, such as silicone, polyurethane, polyacrylate, polyolefin, polyester, polyamide and the like. In some embodiments, the capsule is made of multiple materials. In some embodiments of the disclosure the capsule is made of titanium.

In some embodiments, the capsule is made of a single piece of material. In some embodiments, the capsule is made of multiple pieces of materials, for instance a capsule having a reservoir for holding a therapeutic agent and a stabilizing agent and having a cap holding a membrane as a pathway for release of the therapeutic agent, wherein the cap can be attached to the reservoir by any suitable means, such as welding, gluing, press fitting or using threaded means, or any combination of these.

The capsule may have any suitable size or shape. In some embodiments of the disclosure the capsule is cylindrical, facilitating implantation into the body by means of a tubular implantation device, such as a needle or trocar.

Devices of the disclosure have at least one membrane, as described in this disclosure, attached to the capsule and in fluid contact with the reservoir, wherein the membrane provides a pathway for mass transport of a therapeutic agent included within the reservoir out of that reservoir and into the body of a subject into which the capsule has been implanted. In this disclosure "attached to the capsule" refers to a component being fixed in place with respect to the capsule, and connected to the capsule directly or indirectly, by using any suitable means, including by welding, gluing, press-fitting and by using threaded means, or by any combination of these.

In the case of membranes as described in U.S. Pat. No. 9,814,867, and as illustrated in FIG. 1A, the nanotube membranes are part of an array of nanotubes 103, some of which are still attached to the titanium substrate 104 from which they were grown, and the substrate may be attached to the capsule. At least some of the nanotubes are open on both sides, 105 in FIG. 1A, to allow for mass transport of a therapeutic agent out of the reservoir.

FIG. 1B is a capsule 101b with two reservoirs 102b and two membranes 105b, which allow for mass transport of a therapeutic agent out of the reservoir. In this embodiment, the capsule 101b has at least two arrays of nanotubes 103b, some of which are still attached to the titanium substrate 104b. At least some of the nanotubes are open on both sides 105b in FIG. 1B, to allow for mass transport of a therapeutic agent out of the reservoir.

In certain aspects, the filling capacity of the device may vary. The device may be from about 0.1 cm to about 15 cm in length (L) such as about 0.1 cm, 0.5 cm, 1 cm, 1.5 cm, 2 cm, 2.5 cm, 3 cm, 3.5 cm, 4 cm, 4.5 cm, 5 cm, 5.5 cm, 6 cm, 6.5 cm, 7 cm, 7.5 cm, 8 cm, 8.5 cm, 9 cm, 9.5 cm, 10 cm, 10.5 cm, 11 cm, 11.5 cm, 12 cm, 12.5 cm, 13 cm, 13.5 cm, 14 cm, 14.5 cm, and/or 15 cm. The diameter can vary from 0.1 mm to about 10 mm, such as about 0.1 mm, 0.5 mm, 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, and/or 10 mm. The volume is equal to $\pi r^2 \times L$, where r is the radius or ½ the diameter.

In some embodiments, more than one membrane is present. In some embodiments, more than one type of membrane is present. Membrane types may include dense and porous membranes, including nanoporous membranes and nanotube membranes.

In some embodiments, a titania nanotube membrane is present.

Some devices of the disclosure include at least one polymeric stabilizing agent, for instance stabilizing agents such as described in this disclosure. The stabilizing agent may be present in solid or fluid form. In some instances, the stabilizing agent may be present in mixed forms, such a suspension of a solid form such as a bead or particle of the stabilizing agent in a saturated solution of the stabilizing agent.

Some devices of the disclosure include at least one therapeutic agent, for instance therapeutic agents such as described in this disclosure. The therapeutic agent may be in solid or fluid form. In some instances, the therapeutic agent may be present in mixed forms, such a suspension of a solid form of the therapeutic agent in a saturated solution of the therapeutic agent.

Some devices of the disclosure include a polymeric plug, suitable for sealing one end of a capsule, for instance for sealing one end of a cylindrical capsule. In some embodiments, the plug may be inserted during the manufacturing of the device after a therapeutic agent and a stabilizing agent have been disposed into the reservoir. In some embodiments, the plug forms a septum suitable for piercing with a hollow needle, such as a hypodermic needle, and is attached to the capsule in a position to allow access to the reservoir of the capsule by piercing with the hollow needle. In some embodiments of the disclosure, the septum is used as an access port to the reservoir to facilitate filling the reservoir of the capsule with a fluid form of a therapeutic agent or of a stabilizing agent, or with components of a fluid form of a therapeutic agent or of a stabilizing agent. The septum may be made from any suitable biocompatible material, such as silicone, polyurethane, polyacrylate, polyolefin, polyester, polyamide and the like.

In some embodiments, the device has a capsule configured for implantation, a reservoir, and a nanoporous membrane with a plurality of pores, the membrane being attached to the capsule in fluid contact with the reservoir, wherein the membrane provides a pathway for mass transport of a therapeutic agent out of the reservoir. The membrane may be a nanotube membrane such as described in U.S. Pat. No. 9,814,867. The device includes an insoluble polymeric stabilizing agent, such as described in this disclosure, included within the reservoir and having dimensions larger than the pore size of the membrane, thereby substantially being prevented from being released out of the reservoir through the membrane. The device is configured for introducing into the reservoir a therapeutic agent at the discretion of an operator or medical personnel.

In some embodiments, the device has a capsule configured for implantation, a reservoir, and a nanoporous membrane with a plurality of pores, the membrane being attached to the capsule in fluid contact with the reservoir, wherein the membrane provides a pathway for mass transport of a therapeutic agent out of the reservoir. The membrane may be a nanotube membrane such as described in U.S. Pat. No. 9,814,867. The device includes an insoluble polymeric stabilizing agent, such as described in this disclosure, included within the reservoir and having dimensions larger than the pore size of the membrane, thereby substantially being prevented from being released out of the reservoir through the membrane.

In some devices of the disclosure the stabilizing agent has a plurality of acidic groups. In some embodiments, the acidic groups are present on acrylic acid monomer residues or on methacrylic acid monomer residues, or on a combination of both types of residues.

The device further includes a therapeutic agent, such as described in this disclosure.

In some embodiments, the therapeutic agent is a polypeptide. In some embodiments, the polypeptide is an incretin mimetic. In some embodiments, the incretin mimetic is exenatide.

In some embodiments, the therapeutic agent and the stabilizing agent are present in a substantially dry solid form.

In some embodiments, a solvent for the therapeutic agent is present, creating a solution of at least part of the therapeutic agent. In some embodiments, a solid form of the therapeutic agent is present in a saturated solution of the therapeutic agent.

In an exemplary embodiment, the device has a cylindrical capsule configured for implantation and a reservoir capacity of about 50 microliters. In other instances, a reservoir capacity is about 1 µL to about 1 mL, such as about 1 µL, 25 µL, 50 µL, 75 µL, 100 µL, 125 µL, 150 µL, 175 µL, 200 µL, 225 µL, 250 µL, 275 µL, 300 µL, 325 µL, 350 µL, 375 µL, 400 µL, 425 µL, 450 µL, 475 µL, and/or 500 µL. In other instances, the capacity is about 1 µL-500 µL; or 10 µL-250 µL; or 10 µL-100 µL. The membrane is a titania nanotube membrane attached to one end of the cylindrical capsule.

In one instance, the capsule further has a silicone septum attached to the opposite end of the capsule.

In one instance, the reservoir contains about 10 milligrams of a cross-linked form of methacrylic acid as the stabilizing agent and about 40 microliter of an aqueous solution of 25% (w/w) exenatide as the therapeutic agent, at a pH between 5.0 and 5.5 and with an NaCl concentration of about 154 millimolar.

Some embodiments of the disclosure include methods for preparation of devices of the disclosure. Generally, devices of the disclosure include a capsule having a reservoir for holding a therapeutic agent and for holding a stabilizing agent, and include a membrane providing a mass transport path out of the reservoir for the therapeutic agent, but not for the stabilizing agent. In some devices of the disclosure a pierceable septum is present to facilitate admitting fluid forms of the therapeutic agent and of the stabilizing agent into the reservoir. Device components and methods for their assembly are described in this disclosure.

Methods of preparation of membranes of the disclosure are described in U.S. Pat. Nos. 9,814,867 and 9,770,412.

Methods of preparation of capsules of the disclosure, such as cylindrical tubes made of metals such as stainless steel and titanium, or from polymers such as poly-urethanes and polycarbonate include many well-established machining processes.

Methods of preparation of septa of the disclosure include many polymer processing methods, such as casting from medical grade precursors like medical grade siloxanes.

Some devices of the disclosure include at least one therapeutic agent and at least one stabilizing agent, disposed within the reservoir. Therapeutic agents and stabilizing agents in this disclosure may be combined in any suitable combination in preparing devices of the disclosure, by any suitable means, and in any suitable state.

In some embodiments, a cylindrical capsule is closed at one end, and can be closed at the other end by attaching a membrane. Components of the final formulation are admitted to the reservoir before attaching the membrane, after which the capsule is closed by attaching the membrane. The membrane can be attached by any desirable means, such welding, gluing, press-fitting or using threaded means, or by any combination of these. In some embodiments, all components of the final formulation are admitted before attaching the membrane. In some embodiments, part of the components of the final formulation are added before attaching the membrane, such as dry formulation components, after which fluid formulation components are admitted through the membrane. In order to facilitate admitting fluid components, in some embodiments, the pressure inside the reservoir is reduced before admitting a fluid medium such as described in U.S. patent Ser. No. 10/525,248.

In some embodiments, admitting an aqueous fluid medium is facilitated by including a water-soluble gas in the reservoir, such as described in U.S. Pat. No. 9,511,212.

In some embodiments, a cylindrical capsule has a membrane attached to one end, and can be closed by attaching a septum to the other end. Components of the final formulation can be admitted to the reservoir before attaching the septum, after which the capsule can be closed by attaching the septum. The septum can be attached by any desirable means, such welding, gluing, press-fitting or using threaded means, or by any combination of these. In some embodiments, all components of the final formulation are admitted before attaching the septum. In some embodiments, part of the components of the final formulation are added before attaching the septum, such as dry formulation components, after which fluid formulation components are admitted through the septum by means of a hollow needle. In order to facilitate admitting fluid components, in some embodiments, the pressure inside the reservoir is reduced before admitting a fluid medium such as described in U.S. patent Ser. No. 10/525,248

In some embodiments, admitting an aqueous fluid medium is facilitated by including a water-soluble gas in the reservoir, such as described in U.S. Pat. No. 9,511,212.

Stabilizing agents in a fluid or solid state may be combined with therapeutic agents in a fluid or solid state.

Stabilizing agents and therapeutic agents may be combined in their solid states in a first step, and brought into a fluid state in a later step.

Stabilizing agents and therapeutic agents may be combined in fluid states in a first step, and brought into a solid state in a later step.

Combination of the therapeutic agent and the stabilizing agent may be performed by any suitable method, including dry powder mixing and preparing a fluid mixture of the therapeutic agent and the stabilizing agent.

These options may be combined in any suitable combination and permutation.

The present disclosure provides an implantable drug delivery system capable of delivering the therapeutic agent from the device. In some embodiments, the present disclosure provides an implantable drug delivery system having a capsule suitable for implantation. The implantable drug delivery system can also have a reservoir encapsulated by the capsule, wherein the reservoir contains a pharmaceutical composition of the present disclosure containing a therapeutic agent and a polymer functionalized with a plurality of stabilizing groups. The implantable drug delivery system can also have a membrane in contact with the reservoir, wherein the membrane is the only diffusion pathway out of the reservoir for the therapeutic agent, and wherein the polymer does not substantially diffuse through the membrane.

The capsule can be any capsule that is biocompatible with the body. The capsule can be prepared from any suitable material such as biocompatible materials, metals, polymers and combinations thereof. Useful metals can be pure metals or alloys, and include, but are not limited to, titanium and steel. Polymers useful in the present disclosure include any natural or synthetic polymer that is biocompatible with the body. In some embodiments, the capsule includes titanium.

The capsule can have any suitable shape or size. The capsule can be spherical, elliptical, oblong, circular, or cylindrical, among others.

The device also includes the reservoir which contains the therapeutic agent. Any therapeutic agent is useful in the device of the present disclosure, as described above. The therapeutic agent can be in any suitable form in the reservoir, such as a liquid, a solid or a suspension. Solid forms include, but are not limited to, powders and micronized particles. For example, the powder can be lyophilized.

Any suitable membrane can be used in the implantable drug delivery system of the present disclosure. For example, the membrane can be prepared from any suitable polymer, metal, metal oxide, ceramic inorganic material, or combination thereof. Suitable materials for the membrane include, but are not limited to, silicon, silica, titanium and titania. In some embodiments, the membrane can be titania. Suitable organic materials include any polymeric system that has adequate permeability for $H+$ and $Na+$ ions, and for the therapeutic agent.

Particularly suitable may be hydrogel-based membranes, if necessary as composite materials with an embedded reinforcing mesh. The membrane may be based on any of the hydrogels described above, provided they are formulated with adequate physical integrity, for instance by incorporating cross-linkers. Suitable materials include poly-acrylic hydrogels like poly-hydroxymethyl methacrylate, cross-linked with ethyleneglycoldimethacrylate, and poly-urethane hydrogels like those manufactured by reacting hexamethylenediisocyanate trimers with diols like polyethyleneglycol. In some embodiments, the membrane can be a titania nanotube membrane.

In some embodiments the membrane pores have a diameter of the same order of magnitude as the hydrodynamic diameter of dissolved substances, such as a therapeutic agent in the formulation. In some embodiments, the pores have a diameter smaller than hydrodynamic diameter of dissolved substances in the formulation. Because of the finite size of the pores, such membranes may act as a size cut-off filter for dissolved substances in the formulations of the drug delivery systems.

The membranes of the present disclosure can have any suitable pore size. For example, the membrane pores can have a diameter of at least about 10 µm, 1 µm, 1000 nm, 500 nm, 100 nm, 50 nm, 25, nm, 10, nm at least about 5 nm, or at least about 1 nm. The membrane pores can also have a diameter of from about 1 nm to about 10 µm, or from about 1 nm to about 1 µm, or from about 1 nm to about 500 nm, or from about 1 nm to about 100 nm, or from about 1 nm to about 50 nm.

In some embodiments, the membrane can be a titania nanotube membrane on a titanium substrate, such as that described in PCT Publication No. WO 2013/085951 or U.S. Application Publication No. 2014/0371687. In some embodiments, the pores in the nanotube membranes have diameters in a range of 1-5 times or 1, 2, 3, 4, or 5 times the hydrodynamic radius of the drug molecules diffusing through their aqueous phase. It has been shown that under those conditions drug release rates may be achieved that are independent of the gradient of the concentration of the drug between a reservoir in the drug delivery system and the environment into which the drug is released.

The implantable drug delivery system of the present disclosure can have one or more membranes. For example, the implantable drug delivery system can have 1, 2, 3, 4, or more membranes. The membranes can have the same or different pore diameters. When the implantable drug delivery system has more than one membrane each with the same pore diameter, each membrane can provide a diffusion pathway for the therapeutic agent. Alternatively, the membranes can each have different pore diameters such that one or more of the membranes does not provide a diffusion pathway for the therapeutic agent. In some embodiments, when two membranes are present in the implantable drug delivery system, only one membrane provides a diffusion pathway for the therapeutic agent.

In some embodiments, the present disclosure provides a device having a capsule suitable for implantation. The device also includes a reservoir encapsulated by the capsule, wherein the reservoir is suitable for containing a therapeutic agent. The device also includes a titania nanotube membrane on a titanium substrate, wherein the titanium substrate is attached to the capsule such that the titanium substrate is in contact with the reservoir, wherein the titania nanotube membrane comprises a plurality of titania nanotubes in fluid contact with the reservoir. The device is such that the plurality of titania nanotubes is the only pathway out of the reservoir for the therapeutic agent.

The titania nanotubes are in fluid contact with the reservoir such that the therapeutic agent, whether in liquid, solid or suspension form, can be released from the reservoir and into the titania nanotubes at the titanium substrate, followed by exiting the titania nanotubes at the opposite end and entering the body. The rate of release of the therapeutic agent can be any suitable rate of release, such as zero-order rate of release. In some embodiments, the release of the therapeutic agent from the reservoir and through the titania nanotube membrane is a zero-order rate of release.

The combination of the composition of the present disclosure and the implantable drug delivery system of the present disclosure allow the stabilization of the therapeutic agent of the composition in the reservoir of the implantable drug delivery system. For example, the therapeutic agent can be stabilized by implanting in a patient in need thereof, the drug delivery system of the present disclosure having a composition of the present disclosure in the reservoir, and maintaining a pH inside the reservoir to form a pH differential of at least 0.5 pH units with the pH of the patient's tissue immediately surrounding the implantable drug delivery system. In some embodiments, the present disclosure provides a method of stabilizing a therapeutic agent in a reservoir of an implantable drug delivery system, the method comprising implanting in a patient in need thereof, the implantable drug delivery system comprising a reservoir containing a therapeutic agent and a polymer stabilizing agent comprising a plurality of stabilizing groups that can each be an acid group or a base group, and maintaining the pH inside the reservoir to create a pH differential of at least 0.5 pH units with the pH of the patient's tissue surrounding the implantable drug delivery system.

IV. Membranes

Embodiments of the disclosure include at least one membrane providing a pathway for mass transport of a therapeutic agent out of a reservoir of a device of the disclosure.

A wide variety of membranes can be used in embodiments of the present disclosure.

Membranes of the disclosure include dense and porous membranes; porous membranes include nanoporous membranes and nanotube membranes.

Suitable materials for membranes of the disclosure include organic and inorganic materials, polymers, ceramics, metals, metal oxides and combinations thereof. Suitable materials for the membrane include silicon, silica, titanium and titania.

In some embodiments, the membrane is a nanoporous membrane. In some embodiments, the membrane is a nanotube membrane. In some embodiments, the membrane is a titania nanotube membrane.

Embodiments of the disclosure are particularly useful as sustained delivery devices for therapeutic agents, in which the release of the agents is controlled by a nanoporous membrane.

Some embodiments of the disclosure comprise a titania nanotube membrane, such as described in U.S. Pat. No. 9,814,867. The pore size of membranes of the disclosure can be controlled by processes such as described in U.S. Pat. No. 9,770,412.

Generally, average pore sizes of membranes of the disclosure may be between 1 and 1000 nanometers. In some embodiments, average pore sizes larger than 1000 nanometers may be present. In some embodiments the average pore size is from 1 to 5 nanometers. In some embodiments, the average pore size is from 5 to 10 nanometers. In some embodiments, the average pore size is from 10 to 50 nanometers. In some embodiments, the average pore size is from 50 to 100 nanometers. In some embodiments, the average pore size is from 15 to 40 nanometer. In some embodiments, the average pore size is from 1 to 50 nanometers, for example approximately 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and/or 50. In some embodiments, the average pore size is from 100 to 1000 nanometers. In some embodiments, pore sizes of less than 1 nanometer may be present.

In some embodiments, the membrane pores have a diameter of the same order of magnitude as the hydrodynamic diameter of dissolved substances, such as a therapeutic agent in a formulation. In some embodiments, the pores have a diameter smaller than hydrodynamic diameter of dissolved substances in a formulation. Because of the finite size of the pores, such membranes may act as a size cut-off filter for dissolved substances in the formulations of the drug delivery systems.

In some embodiments, the membrane pores have diameters in a range of 1-5 times or 1, 2, 3, 4, or 5 times or even more times the size of the molecular diameter of the drug molecules diffusing through their aqueous phase. In some embodiments, the membrane pores have diameters, as described in U.S. patent application Ser. No. 16/204,890. It has been shown that under those conditions drug release rates may be achieved that are not controlled by a concentration gradient between the reservoir and the environment into which the drug is released as would be seen in typical Fickian diffusion, and that may approach a more constant release rate over time.

The membrane pores are in fluid contact with the therapeutic agent in the reservoir, such that molecules of the therapeutic agent are able to diffuse into and out of the pores and into an environment surrounding the device. The profile of the release rate over time may be any desired profile. In some embodiments, the profile is a declining profile, in accordance with regular Fickian diffusion out of the reservoir. In some embodiments, the release rate profile is non-Fickian, like a constant rate or near-constant rate profile. Constant rate profiles are sometimes referred to as zero-order release rate profiles. Some embodiments have a spike in drug release rate at early time points in the profile. Some embodiments have slow ramp up of release rates at early time points in the release rate profile.

The implantable drug delivery system of the present disclosure can have one or more membranes (See, FIG. 1B). For example, the implantable drug delivery system can have 1, 2, 3, 4, or more membranes. Membrane types include nanoporous and non-porous membranes. Different nanoporous membranes can have the same or different pore diameters. When the implantable drug delivery system has more than one membrane each with the same pore diameter, each membrane can provide a diffusion pathway for the therapeutic agent.

Alternatively, the membranes can each have different pore diameters such that one or more of the membranes does not provide a diffusion pathway for the therapeutic agent. In some embodiments, when two membranes are present in the implantable drug delivery system, only one membrane provides a diffusion pathway for the therapeutic agent.

V. Micro-Stabilizer Composition

The present disclosure provides a composition for stabilizing a therapeutic agent by combining the therapeutic agent with a polymer stabilizing group. The polymer stabilizing group can be any suitable stabilizing group, such as a buffering group. For example, the present disclosure provides a composition containing a therapeutic agent and a polymeric buffering agent capable of buffering an environment to stabilize the therapeutic agent at a particular pH or range of pH values. The buffering agent can be any suitable material, such as a polymer, hydrogel, or other material, that provides the properties of a buffer. In some embodiments, the present disclosure provides a pharmaceutical composition having a therapeutic agent, and a polymeric stabilizing agent comprising a polymer and a plurality of stabilizing groups. In some embodiments, the present disclosure provides a pharmaceutical composition having a therapeutic agent, and a polymeric buffering agent comprising a polymer including ionizable groups such as a plurality of acid groups or a plurality of base groups.

Any suitable therapeutic agent can be used in the compositions of the present disclosure, and are described in greater detail below. In some embodiments, the therapeutic agent can be a peptide, a polypeptide or a protein. In some embodiments, the therapeutic agent can be a peptide. In some embodiments, the therapeutic agent can be beta-glucocerobrosidase, interferon alpha, interferon beta, agasidase alpha, agasidase beta, exenatide, nutropin/somatropin, factor VIII, fondaparinux, aldesleukinand, risperidone, forigerimod, NP fusion proteins, IL-12, a melanocyte stimulating hormone, or bapineuzumab. In some embodiments, the therapeutic agent can be exenatide, octreotide or fluphenazine. In some embodiments, the therapeutic agent can be exenatide.

In some embodiments, the stabilizing excipient has an oligomeric or polymeric molecular backbone structure. The oligomeric or polymeric backbones may be based on homopolymeric or copolymeric structures. The molecules can have any suitable architecture, including, but not limited to, linear, branched, comb, star, hyperbranched, cross-linked and dendritic architectures. Architectures that adopt a more spherical or globular shape can have certain advantages, and can include branched, comb, star, hyperbranched and dendritic polymers. In some embodiments the molecular structure is a cross-linked structure.

The polymeric buffering agent can include any suitable polymer. Acidic polymers useful for the disclosure include polyacids based on carboxylic acid groups, like polyacrylic acid and polymethacrylic acid, on sulfonic acids groups like polystyrene sulfonic acid and polyvinyl sulfonic acid, and on phosphonic acid groups, like polyvinyl phosphonic acid and polystyrene phosphonic acid. Basic polymers useful for the disclosure are often based on amine structures, including primary, secondary, tertiary and quaternary amines. Examples are polyvinyl amine and polystyrene amine and their secondary, tertiary and quaternary derivatives. Other polymers useful as the biocompatible support can include, but are not limited to, polyphosphazenes, polyanhydrides, polyacetals, poly(ortho esters), polyphosphoesters, polycaprolactones, polyurethanes, polylactides, polycarbonates, polyamides, and polyethers, and blends/composites/copolymers thereof. Representative polyethers include, but are not limited to, Poly(ethylene glycol) (PEG), poly(propylene glycol) (PPG), triblock Pluronic ([PEG]n-[PPG]m-[PEG]n), PEG diacrylate (PEGDA) and PEG dimethacrylate (PEGDMA). Other polymers useful in the present disclosure include, but are not limited to, poly(ethylene glycol), polystyrene, poly(amidoamine) dendrimers, and others. The polymers can have any suitable architecture, including, but not limited to, linear, branched, comb, star, hyperbranched, cross-linked and dendritic. Architectures that adopt a more spherical or globular shape can have certain advantages, and can include branched, comb, star, hyperbranched and dendritic polymers. In some embodiments, the polymer can be a dendrimeric polymers based on poly-amido-amine structures.

Stabilizing functional groups of a chemical nature analogous to the low molecular weight stabilizing excipients mentioned above may be attached to the backbone structure of the oligomeric or polymeric excipient, in some embodiments the attachment is through a covalent chemical link; in some embodiments the attachment is through a non-covalent link, such as a salt formation or complexation. Typical stabilizing functional groups include acids, bases, buffers, anti-oxidants, anti-aggregation agents, and anti-microbials. In some embodiments, each stabilizing group can independently be an acid group, a base group, an anti-oxidant, an anti-microbial, an anti-biotic, a protein clustering agent, or a protein declustering agent.

The polymer can include any suitable functional group to provide the buffering functionality of the polymeric buffering agent. For example, the polymer can be functionalized with an ionizable group such as an acid group or a base group. In some embodiments, each stabilizing group can independently be an acid group or a base group. Representative acid groups include, but are not limited to, carboxylic acid, peroxy acid, amino acid, sulfonic acid, sulfinic acid, phosphonic acid, phosphinic acid, thiol and phenol. In some embodiments, the acid group can be carboxylic acid, amino acid, thiol, and phenol. In some embodiments, the acid groups can be carboxylic acids. For basic groups, amines, pyridines, guanidine, and the like can be used.

Representative stabilizing acid groups include, but are not limited to, carboxylic acid, peroxy acid, amino acid, sulfonic acid, sulfinic acid, phosphonic acid, phosphinic acid.

Representative stabilizing basic groups include, but are not limited to, primary, secondary, tertiary and quaternary amines. The acidic or basic groups of the polymers described above may serve as a basis for further derivatization of the polymers with other stabilizing end groups. Alternatively, polymers with other reactive groups, such as polyvinyl alcohol, may be used for attachment of stabilizing end group, for instance through esterification of a hydroxyl group on the poly-vinyl alcohol with a carboxylic acid group on a stabilizing moiety.

Alternatively, or additionally, the polymer can be functionalized with other stabilizing end groups, such as anti-oxidants. Anti-oxidants can include natural anti-oxidants, such as carotenoids, vitamin E and vitamin C, and synthetic anti-oxidants, like butylated hydroxytoluene, butylated hydroxyanisol and propyl gallate. The end groups of the polymers can be functionalized many different ways, and most anti-oxidants possess multiple functional groups, leaving one with ordinary skills in the art of synthetic chemistry with a variety of options for chemical coupling reactions between the dendrimer and the anti-oxidants.

Anti-oxidative end groups can be based on natural anti-oxidants, such as carotenoids, vitamin E and vitamin C, and on synthetic anti-oxidants, like butylated hydroxytoluene, butylated hydroxyanisol and propyl gallate.

For instance, an anti-oxidant conjugate may be produced through esterification of an acid group on a polymer with the phenyl hydroxyl group of tocopherol, or through esterification with the terminal hydroxyl group of retinol.

Similarly, end groups of the polymers can be functionalized with molecules that promote or reduce clustering of protein molecules in the formulation. Clustering can typically be promoted by compounds enhancing the internal structure of liquid water, such as many carbohydrates, including poly-saccharides, while declustering is often promoted by compounds breaking up internal water structures, such as surfactants. Suitable surfactants include ionic surfactants such a long chain fatty acid salts, or non-ionic surfactants such as the Tween, Brij and Triton series.

Also, in cases where microbial control is desired, the polymer end groups can be functionalized with antibiotics, for instance beta-lactams or aminoglycosides, or with anti-bacterials like quaternary ammonium ions or silver compounds.

Similarly, esterification with one of the phenyl hydroxyl groups of hexachlorophene may be used to produce a oligomer or polymer with anti-bacterial properties. Also, the polymer acid or base groups can be functionalized with antibiotics, for instance beta-lactams or aminoglycosides, or with anti-bacterial like quaternary ammonium ions or silver compounds.

Representative base groups of the polymeric buffering agent include, but are not limited to, amine, alkylamine, arylamine, amide, hydroxy, hydroxy-amine, cyano, and carboxylate. In some embodiments, the base group can be hydroxy, cyano, amine or carboxylate. In some embodiments, the base group can be carboxylate.

In some embodiments, the polymer can be a dendrimer. Dendrimers are characterized by having a core, monomer branching units, and a plurality of end groups. Any suitable dendrimer can be useful in the compositions of the present disclosure. Representative dendrimers include, but are not limited to, poly(amidoamine) dendrimers, poly(benzylether) dendrimers, poly(alkylether) dendrimers, etc. Poly(amidoamine) dendrimers are also referred to as PAMAM dendrimers. In some embodiments, the polymer can be a poly(amidoamine) dendrimer.

PAMAM dendrimers are characterized by having an amido-amine monomer branching unit. Any suitable core can be used for the PAMAM dendrimers of the present disclosure. For example, the core can be an alkylenediamine such as ethylene diamine. Other cores are known to one of skill in the art. The end groups of the PAMAM dendrimers can be any suitable end group. Representative end groups include, but are not limited to, amine, alkylamine, alkyl, alkylhydroxy, carboxylate, etc. In some embodiments, the end groups of the poly(amidoamine) dendrimer include sodium carboxylate.

Dendrimers can be prepared by a variety of methods, such as by step-wise, consecutive addition of monomeric units to a growing polymer backbone. Each additional addition of a set of monomers gives rise to what is referred to as a new "generation." The dendrimers useful in the present disclosure can be of any suitable generation. For example, the dendrimer can be Generation 1, 2, 3, 4, 5, 6, 7, 8, 9, 10, or greater. The higher generation dendrimers can have larger molecular diameters as compared to lower generation dendrimers, so higher generation dendrimers can be preferred. When the dendrimer is a poly(amidoamine) dendrimer, the dendrimer can be any suitable generation. In some embodiments, the poly(amidoamine) dendrimer can be at least a Generation 3 dendrimer. In some embodiments, the poly(amidoamine) dendrimer can be at least a Generation 5 dendrimer. In some embodiments, the poly(amidoamine) dendrimer can be at least a Generation 7 dendrimer. In some embodiments, the poly(amidoamine) dendrimer can be at least a Generation 9 dendrimer.

The polymers of the present disclosure can be of any suitable molecular diameter. For example, the polymer can have a molecular diameter of at least 1 nm, or of at least 2, 3, 4, 5, 6, 7, 8, 9, or of at least 10 nm. In some embodiments, the polymer can have a molecular diameter of at least 3 nm. In some embodiments, the polymer can have a molecular diameter of at least 5 nm.

The polymers of the present disclosure can be obtained via commercial sources or can be prepared by any means known to one of skill in the art.

The table below shows a number of characteristic properties of PAMAM dendrimers of increasing generation, such as those produced by Dendritech Inc., from Midland, Michigan.

| Generation | Molecular Weight | Measured Diameter (nm) | Surface Groups |
|---|---|---|---|
| 0 | 517 | 1.5 | 4 |
| 1 | 1,430 | 2.2 | 8 |
| 2 | 3,256 | 2.9 | 16 |
| 3 | 6,909 | 3.6 | 32 |
| 4 | 14,215 | 4.5 | 64 |
| 5 | 28,826 | 5.4 | 128 |
| 6 | 58,048 | 6.7 | 256 |
| 7 | 116,493 | 8.1 | 512 |
| 8 | 233,383 | 9.7 | 1024 |
| 9 | 467,162 | 11.4 | 2048 |
| 10 | 934,720 | 13.5 | 4096 |

The amino surface groups or end groups of the polymer chains can be used to derivatize the molecule through reactions like amide- or Schiff's base formation. Derivatives produced in this and other manners include amidoethanol-, succinamic acid-, carboxylate-, and hydrophobic end groups. These end groups can be used as a basis for further derivatization.

The pharmaceutical composition of the present disclosure can have any suitable pH. For example, the pH can be acidic, i.e., less than 7, when the polymeric buffering agent includes acid groups. When the compositions are acidic, the pH of the compositions of the present disclosure can have a pH of less than 7, or a pH of from about 2 to 7, or from about 3 to 7, or from about 4 to about 6. In some embodiments, the pH of the composition can be less than 7. In some embodiments, the pH of the composition can be from about 3 to 7. In some embodiments, the pH of the composition can be from about 4 to about 6. When the compositions are basic, the pH of the composition can be greater than 7, such as when the polymeric buffering agent includes base groups. The compositions of the present disclosure can have a pH of greater than 7, or a pH of from 7 to about 12, or from 7 to about 11, or from about 8 to about 10.

In many instances, drug formulations suitable for use in an implantable controlled release drug delivery system require the presence of stabilizing excipients to maintain stability of the drug over the duration of implantation. Typical stabilizing excipients include acids, bases, buffers, anti-aggregation agents (for proteins), anti-oxidants and anti-microbials. Frequently, such stabilizing excipients are low molecular weight compounds. In cases where the drug, also referred to as the Active Pharmaceutical Ingredient (API) is significantly larger than the excipients, and where the pore size of the membrane is tailored towards controlling release of the drug, the low molecular weight excipients may be released too fast. The stability of the active agent can be measured by any suitable means. For example, Example 16 describes a method of determining the stability of the active agent using HPLC, with and without the stabilizing polymer PAMAM-COOH.

In some embodiments, formulations according to the disclosure comprise a therapeutic agent and a stabilizing excipient, wherein the stabilizing excipient has a molecular dimension in solution that is of the same order of magnitude as a corresponding molecular dimension of the therapeutic agent in the solution. Any appropriate measure of molecular dimension may be used for the comparison, such as radius of gyration, Stokes radius, or, in aqueous solutions, hydrodynamic radius.

In some embodiments the excipient has a molecular dimension in solution at least equal to the size of the molecular dimension of the therapeutic agent in the solution; in preferred embodiments the excipient has a molecular dimension in solution at least 2 times the size of the molecular dimension of the therapeutic agent in the solution; in most preferred embodiments the excipient has a molecular dimension in solution at least 5 times the size of the molecular dimension of the therapeutic agent in the solution.

Solutions in this context may be aqueous, organic, or mixed aqueous organic solutions. By tailoring the molecular dimensions of the excipient molecules to the dimensions of the therapeutic agent, their release may be reduced to levels that are appropriate to maintain sufficient levels of excipient in the formulation for a required period of time. By selecting excipients that are larger than the pore size of the membranes of their delivery systems, their release may be substantially prevented.

In some embodiments, the present disclosure provides a pharmaceutical composition comprising a therapeutic agent and a polymeric stabilizing agent comprising a polymer and a plurality of stabilizing groups. In some embodiments, the pharmaceutical composition consists essentially of a therapeutic agent and a polymeric stabilizing agent consisting essentially of a polymer and a plurality of stabilizing groups. In some embodiments, the pharmaceutical composition consists of a therapeutic agent and a polymeric stabilizing agent consisting of a polymer and a plurality of stabilizing groups.

In some embodiments, the pharmaceutical composition comprises exenatide and a PAMAM-COOH dendrimer. In some embodiments, the pharmaceutical composition consists essentially of exenatide and a PAMAM-COOH dendrimer. In some embodiments, the pharmaceutical composition consists of exenatide and a PAMAM-COOH dendrimer. In some embodiments, the pharmaceutical composition comprises exenatide, a PAMAM-COOH dendrimer and a PAMAM-methionine dendrimer. In some embodiments, the pharmaceutical composition comprises exenatide, a PAMAM-COOH dendrimer, a PAMAM-methionine dendrimer and a PAMAM-silver sulfadizaine dendrimer. In some embodiments, the pharmaceutical composition comprises exenatide, a PAMAM-COOH dendrimer and a PAMAM-tocopherol dendrimer. In some embodiments, the pharmaceutical composition comprises exenatide, a PAMAM-COOH dendrimer, a PAMAM-tocopherol dendrimer and a PAMAM-sulfur sulfadiazine dendrimer.

In some embodiments, the pharmaceutical composition comprises octreotide, a PAMAM-COOH dendrimer and a PAMAM-methionine dendrimer. In some embodiments, the pharmaceutical composition comprises octreotide, a PAMAM-COOH dendrimer, a PAMAM-methionine dendrimer and a PAMAM-hexachlorophene dendrimer. In some embodiments, the pharmaceutical composition comprises octreotide, a PAMAM-COOH dendrimer and a PAMAM-retinol dendrimer. In some embodiments, the pharmaceutical composition comprises octreotide, a PAMAM-COOH dendrimer, a PAMAM-retinol dendrimer and a PAMAM-sulfur sulfadiazine dendrimer.

In some embodiments, the pharmaceutical composition comprises fluphenazine and a PAMAM-tocopherol dendrimer.

The compositions of the present disclosure can be prepared by any means known to one of skill in the art.

VI. Therapeutic Agents

Some embodiments of the disclosure include low molecular weight therapeutic agents, sometimes referred to as "small molecule drugs." Some embodiments of the disclosure include high molecular weight therapeutic agents, like peptides and proteins, carbohydrates and nucleic acids, and combinations thereof, like glycoproteins.

Some embodiments of the disclosure include more than one type of therapeutic agent. In one instance, a first therapeutic agent is in a first reservoir 102b of FIG. 1B on the left and a second therapeutic agent in a second reservoir as in 102b on the right of FIG. 1B.

Therapeutic agents of the disclosure may be present in any desired state, including fluid and solid forms.

Some embodiments of the disclosure comprise a therapeutic agent in need of stabilization. In some embodiments, stabilization is provided by pH-controlling agents.

Stabilization mechanisms provided by embodiments of the disclosure include chemical or physical mechanisms, as well as combinations of both.

Many polypeptides include asparagine and/or glutamine residues, which are susceptible to degradation by deamidation reactions. The rate of these deamidation reactions is pH dependent, and typically starts to accelerate rapidly above pH levels around or about 6.0 to about 6.5. Likewise, other degradation reactions, such as isomerization and racemization may be pH dependent and may be controllable by embodiments of the disclosure.

Many polypeptides have a tendency to aggregate in a reversible or irreversible form, and frequently the propensity to aggregation reaches a maximum at the isoelectric point of the polypeptide. By maintaining pH levels away from the isoelectric point embodiments of the disclosure may reduce the tendency for polypeptide aggregation.

Any suitable therapeutic agent can be incorporated into embodiments of the disclosure. For example, the therapeutic agent can be a small molecule drug, such as one having a molecular weight of less than about 1000 g/mol, or less than about 750 g/mol, or less than about 500 g/mol. In some embodiments, the therapeutic agent can be tacrine, memantine, rivastigmine, galantamine, donepezil, levetiracetam, repaglinide, atorvastatin, alefacept, tadalafil, vardenafil, sildenafil, fosamprenavir, oseltamivir, valacyclovir and valganciclovir, abarelix, adefovir, alfuzosin, alosetron, amifostine, amiodarone, aminocaproic acid, aminohippurate sodium, aminoglutethimide, aminolevulinic acid, aminosalicylic acid, amlodipine, amsacrine, anagrelide, anastrozole, aprepitant, aripiprazole, asparaginase, atazanavir, atomoxetine, anthracyclines, bexarotene, bicalutamide, bleomycin, bortezomib, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daptomycin, daunorubicin, deferoxamine, dexamethasone, diclofenac, diethylstilbestrol, docetaxel, doxorubicin, dutasteride, eletriptan, emtricitabine, enfuvirtide, eplerenone, epirubicin, estramustine, ethinyl estradiol, etoposide, exemestane, ezetimibe, fentanyl, fexofenadine, fludarabine, fludrocortisone, fluorouracil, fluoxymesterone, flutamide, fluticazone, fondaparinux, fulvestrant, gamma-hydroxybutyrate, gefitinib, gemcitabine, epinephrine, L-Dopa, hydroxyurea, icodextrin, idarubicin, ifosfamide, imatinib, irinotecan, itraconazole, goserelin, laronidase, lansoprazole, letrozole, leucovorin, levamisole, lisinopril, lovothyroxine sodium, lomustine, mechlorethamine, medroxyprogesterone, megestrol, melphalan, memantine, mercaptopurine, mequinol, metaraminol bitartrate, methotrexate, metoclopramide, mexiletine, miglustat, mitomycin, mitotane, mitoxantrone, modafinil, naloxone, naproxen, nevirapine, nicotine, nilutamide, nitazoxanide, nitisinone, norethindrone, octreotide, oxaliplatin, palonosetron, pamidronate, pemetrexed, pergolide, pentostatin, pilcamycin, porfimer, prednisone, procarbazine, prochlorperazine, ondansetron, palonosetron, oxaliplatin, raltitrexed, rosuvastatin, sirolimus, streptozocin, pimecrolimus, sertaconazole, tacrolimus, tamoxifen, tegaserod, temozolomide, teniposide, testosterone, tetrahydrocannabinol, thalidomide, thioguanine, thiotepa, tiotropium, topiramate, topotecan, treprostinil, tretinoin, valdecoxib, celecoxib, rofecoxib, valrubicin, vinblastine, vincristine, vindesine, vinorelbine, voriconazole, dolasetron, granisetron, formoterol, fluticasone, leuprolide, midazolam, alprazolam, amphotericin B, podophylotoxins, nucleoside antivirals, aroyl hydrazones, sumatriptan, eletriptan; macrolides such as erythromycin, oleandomycin, troleandomycin, roxithromycin, clarithromycin, davercin, azithromycin, flurithromycin, dirithromycin, josamycin, spiromycin, midecamycin, loratadine, desloratadine, leucomycin, miocamycin, rokitamycin, andazithromycin, and swinolide A; fluoroquinolones such as ciprofloxacin, ofloxacin, levofloxacin, trovafloxacin, alatrofloxacin, moxifloxacin, norfloxacin, enoxacin, gatifloxacin, gemifloxacin, grepafloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents like penicillin G, penicillin V; penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, and ertapenem, pentamidine isetionate, albuterol sulfate, lidocaine, metaproterenol sulfate, beclomethasone diprepionate, triamcinolone acetamide, budesonide acetonide, salmeterol, ipratropium bromide, flunisolide, cromolyn sodium, and ergotamine tartrate; taxanes such as paclitaxel; SN-38, or tyrphostines. Therapeutic agents can also be aminohippurate sodium, amphotericin B, doxorubicin, aminocaproic acid, aminolevulinic acid, arninosalicylic acid, metaraminol bitartrate, pamidronate disodium, daunorubicin, levothyroxine sodium, lisinopril, cilastatin sodium, mexiletine, cephalexin, deferoxamine, or amifostine.

Other therapeutic agents useful in the present disclosure can include peptides, polypeptides, proteins, antibodies, etc. In some embodiments, the therapeutic agent can be erythropoietin, granulocyte colony stimulating factor (G-CSF), GM-CSF, interferon alpha, interferon beta, human growth hormone, imiglucerase, or RANK ligand. In other embodiments, the therapeutic agents can be Aβ, agalsidase, alefacept, alkaline phosphatase, aspariginase, amdoxovir (DAPD), antide, becaplermin, botulinum toxin including types A and B and lower molecular weight compounds with botulinum toxin activity, calcitonins, CD1d, cyanovirin, denileukin diftitox, erythropoietin (EPO), EPO agonists, dornase alpha, erythropoiesis stimulating protein (NESP), coagulation factors such as Factor V, Factor VII, Factor VIIa, Factor VIII, B domain deleted Factor VIII, Factor IX, Factor X, Factor XII, Factor XIII, von Willebrand factor; ceredase, Fc gamma r2b, cerezyme, alpha-glucosidase, N-Acetylgalactosamine-6-sulfate sulfatase, collagen, cyclosporin, alpha defensins, beta defensins, desmopressin, GLP-1 analogs such as exendin-4 (EXENATIDE®), cytokines, cytokine receptors, granulocyte colony stimulating factor (G-CSF), thrombopoietin (TPO), alpha-1 proteinase inhibitor, elcatonin, granulocyte macrophage colony stimulating factor (GM-CSF), fibrinogen, filgrastim, growth hormones human growth hormone (hGH), somatropin, growth hormone releasing hormone (GHRH), GRO-beta, GRO-beta antibody, bone morphogenic proteins such as bone morphogenic protein-2, bone morphogenic protein-6, parathyroid hormone, parathyroid hormone related peptide, OP-1; acidic fibroblast growth factor, basic fibroblast growth factor, Fibroblast Growth Factor 21, CD40 ligand, ICOS, CD28, B7-1, B7-2, TLR and other innate immune receptors, heparin, human serum albumin, low molecular weight heparin (LMWH), interferon alpha, interferon beta, interferon gamma, interferon omega, interferon tau, consensus interferon; interleukins and interleukin receptors such as interleukin-1 receptor, interleukin-2, interleukin-2 fusion proteins, interleukin-1 receptor antagonist, interleukin-3, interleukin-4, interleukin-4 receptor, interleukin-6, interleukin-8, interleukin-12, interleukin-17, interleukin-21, interleukin-13 receptor, interleukin-17 receptor; lactoferrin and lactoferrin fragments, luteinizing hormone releasing hormone (LHRH), insulin, pro-insulin, insulin analogues, amylin, C-peptide, somatostatin, somatostatin analogs including octreotide, vasopressin, follicle stimulating hormone (FSH), imiglucerase, influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), trk A, trk B, osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF) (e.g., TNF-α and TNF-β), TNF receptors (e.g., TNF-α receptor and TNF-β receptor), CTLA4, CTLA4 receptor, monocyte chemoattractant protein-1, endothelial growth factors, parathyroid hormone (PTH), PTHrP, glucagon-like peptide, somatotropin, thymosin alpha 1, rasburicase, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosphonates, respiratory syncytial virus antibody, cystic fibrosis transmembrane regulator (CFTR) gene, deoxyribonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, adalimumab, afelimomab, alemtuzumab, antibody to B-lymphocyte, atlizumab, basiliximab, bevacizumab, biciromab, bertilimumab, CDP-484, CDP-571, CDP-791, CDP-860, CDP-870, cetuximab, clenoliximab, daclizumab, eculizumab, edrecolomab, efalizumab, epratuzumab, fontolizumab, gavilimomab, gemtuzumab ozogamicin, ibritumomab tiuxetan, infliximab, inolimomab, keliximab, labetuzumab, lerdelimumab, olizumab, radiolabeled lym-1, metelimumab, mepolizumab, mitumomab, muromonad-CD3, nebacumab, natalizumab, odulimomab, omalizumab, oregovomab, palivizumab, pemtumomab, pexelizumab, rhuMAb-VEGF, rituximab, satumomab pendetide, sevirumab, siplizumab, tositumomab, $I^{131}$ tositumomab, trastuzumab, tuvirumab, visilizumab, or fragments or mimetics thereof.

In other embodiments, the therapeutic agent can be a fusion protein. For example, the therapeutic agent can be an immunoglobulin or portion of an immunoglobulin fused to one or more certain useful peptide sequences. The therapeutic agent can also contain an antibody Fc fragment.

In some embodiments, the therapeutic agent can be a human protein or human polypeptide, for example, a heterologously produced human protein or human polypeptide. Numerous proteins and polypeptides are disclosed herein for which there is a corresponding human form (i.e., the protein or peptide is normally produced in human cells in the human body). Examples of human proteins include, without limitation, human antibodies, human enzymes, human hormones and human cytokines such as granulocyte colony stimulation factor, granulocyte macrophage colony stimulation factor, interferons (e.g., alpha interferons and beta interferons), human growth hormone and erythropoietin.

Other examples of therapeutic agents include, without limitation, factor VIII, b-domain deleted factor VIII, factor VIIa, factor IX, factor X, anticoagulants; hirudin, alteplase, tpa, reteplase, tpa, tpa-3 of 5 domains deleted, insulin, insulin lispro, insulin aspart, insulin glargine, long-acting insulin analogs, complement C5, hgh, glucagons, tsh, follitropin-beta, fsh, gm-csf, pdgh, ifn alpha2, ifn alpha2a, ifn alpha2b, inf-alpha1, consensus ifn, ifn-beta, ifn-beta 1b, ifn-beta 1a, ifn-gamma (e.g., 1 and 2), ifh-lambda, ifn-delta, it-2, it-11, hbsag, ospa, murine mab directed against t-lymphocyte antigen, murine mab directed against tag-72, tumor-associated glycoprotein, fab fragments derived from chimeric mab directed against platelet surface receptor gpII(b)/III (a), murine mab fragment directed against tumor-associated antigen ca125, lysyl oxidase, LOX2, murine mab fragment directed against human carcinoembryonic antigen, cea, murine mab fragment directed against human cardiac myosin, murine mab fragment directed against tumor surface antigen psma, murine mab fragments (fab/fab2 mix) directed against hmw-maa, murine mab fragment (fab) directed against carcinoma-associated antigen, mab fragments (fab) directed against nca 90, a surface granulocyte nonspecific cross reacting antigen, chimeric mab directed against cd20 antigen found on surface of b lymphocytes, humanized mab directed against the alpha chain of the il2 receptor, chimeric mab directed against the alpha chain of the il2 receptor, chimeric mab directed against tnf-alpha, humanized mab directed against an epitope on the surface of respiratory synctial virus, humanized mab directed against her 2, human epidermal growth factor receptor 2, human mab directed against cytokeratin tumor-associated antigen anti-ctla4, chimeric mab directed against cd 20 surface antigen of b lymphocytes dornase-alpha dnase, beta glucocerebrosidase, tnf-alpha, il-2-diptheria toxin fusion protein, tnfr-lgg fragment fusion protein laronidase, dnaases, alefacept, darbepoetin alpha (colony stimulating factor), tositumomab, murine mab, alemtuzumab, rasburicase, agalsidase beta, teriparatide, parathyroid hormone derivatives, adalimumab (lgg1), anakinra, biological modifier, nesiritide, human b-type natriuretic peptide (hbnp), colony stimulating factors, pegvisomant, human growth hormone receptor antagonist, recombinant activated protein c, omalizumab, immunoglobulin e (lge) blocker, lbritumomab tiuxetan, ACTH, glucagon, somatostatin, somatotropin, thymosin, parathyroid hormone, pigmentary hormones, somatomedin, erythropoietin, luteinizing hormone, chorionic gonadotropin, hypothalmic releasing factors, etanercept, antidiuretic hormones, prolactin and thyroid stimulating hormone.

Further examples of therapeutic agents include, but are not limited, to HERCEPTIN™ (Trastuzumab) (Genentech, CA) which is a humanized anti-HER2 monoclonal antibody for the treatment of patients with metastatic breast cancer; REOPRO™ (abciximab) (Centocor) which is an anti-glycoprotein IIb/IIIa receptor on the platelets for the prevention of clot formation; ZENAPAX™ (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath; Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD2O IgG1 antibody (IDEC Pharm/Genentech, Roche/Zettyaku); LYMPHOCIDE™ which is a humanized anti-CD22 IgG antibody (Immunomedics); ICM3 is a humanized anti-ICAM3 antibody (ICOS Pharm); IDEC-114 is a primate anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (CS) antibody (Alexion Pharm); D2E7 is a humanized anti-TNF-α antibody (CATI-BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); CAT-152, a human anti-TGF-β$_2$ antibody (Cambridge Ab Tech); Cetuximab (BMS) is a monoclonal anti-EGF receptor (EGFr) antibody; Bevacizuma (Genentech) is an anti-VEGF human monoclonal antibody; Infliximab (Centocore, JJ) is a chimeric (mouse and human) monoclonal antibody used to treat autoimmune disorders; Gemtuzumab ozogamicin (Wyeth) is a monoclonal antibody used for chemotherapy; and Ranibizumab (Genentech) is a chimeric (mouse and human) monoclonal antibody used to treat macular degeneration.

Other antibodies, such as single domain antibodies are also useful in the present disclosure. A single domain antibody (sdAb, called Nanobody by Ablynx) is an antibody fragment consisting of a single monomeric variable antibody domain. Like a whole antibody, the sdAb is able to bind selectively to a specific antigen. With a molecular weight of only 12-15 kDa, single domain antibodies are much smaller than common antibodies (150-160 kDa). A single domain antibody is a peptide chain of about 110 amino acids in length, comprising one variable domain (VH) of a heavy chain antibody, or of a common IgG.

In some embodiments, the therapeutic agent can be a peptide, polypeptide, or protein. In some embodiments, the therapeutic agent can be beta-glucocerobrosidase, interferon alpha, interferon beta, agasidase alpha, agasidase beta, exenatide, nutropin/somatropin, factor VIII, fondaparinux, aldesleukinand, risperidone, forigerimod, NP fusion proteins, IL-12, a melanocyte stimulating hormone, or bapineuzumab. In some embodiments, the therapeutic agent can be exenatide.

In certain instances, the amount therapeutic agent is between 0.1% to about 50% w/w of the formulation within the reservoir such as approximately 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, and/or 40% w/w. In certain instances, the amount of therapeutic agent is between 1% to about 30% w/w of the formulation. In certain instances, the amount of therapeutic agent is between 1% to about 20% w/w of the formulation. In certain instances, the amount of therapeutic agent is between 1% to about 10% w/w of the formulation.

In certain instances, the amount of therapeutic agent in a reservoir is about 1.0 mg to 1000 mg or even higher such as up to 10 grams. In certain instances, about 1 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, and/or 1000 mg. In certain instances, the amount of therapeutic agent is about 1.0 mg to 100 mg; or about 1.0 mg to 40 mg; or about 1.0 mg to 30 mg; or about 1.0 mg to 20 mg; or about 1.0 mg to 10 mg; or about 0.1 to about 10 mg such as approximately 0.5 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, and/or 10 mg.

In some embodiments of the device and formulation, the therapeutic agent is an incretin mimetic.

Incretin mimetics of the disclosure include, but are not limited to, exenatide, liraglutide, semaglutide, cotadutide, dulaglutide, albiglutide, lixisenatide, sitagliptin, saxagliptin, alogliptin, and linagliptin. In some embodiments of the disclosure more than one incretin mimetic may be present. In some embodiments of the disclosure the incretin mimetic is exenatide.

In certain instances, the amount incretin mimetic is between 0.1% to about 50% w/w of the formulation such as approximately 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, and/or 40% w/w. In certain instances, the amount of incretin mimetic is between 1% to about 30% w/w of the formulation. In certain instances, the amount of incretin mimetic is between 1% to about 20% w/w of the formulation. In certain instances, the amount of incretin mimetic is between 1% to about 10% w/w of the formulation.

In certain instances, the amount of exenatide is between 0.1% to about 40% w/w of the formulation such as approximately 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, and/or 40% w/w. In certain instances, the amount of exenatide is between 1% to about 30% w/w of the formulation. In certain instances, the amount of exenatide is between 1% to about 20% w/w of the formulation. In certain instances, the amount of exenatide is between 1% to about 10% w/w of the formulation.

In certain instances, the therapeutic agent is an incretin memetic such as exenatide. In certain instances, the amount of incretin memetic such as exenatide in a reservoir is about 1.0 mg to 1000 mg or even higher such as up to 10 grams. In certain instances, about 1 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, and/or 1000 mg. In certain instances, the amount of incretin memetic such as exenatide is about 1.0 mg to 100 mg; or about 1.0 mg to 40 mg; or about 1.0 mg to 30 mg; or about 1.0 mg to 20 mg; or about 1.0 mg to 10 mg; or about 0.1 to about 10 mg such as approximately 0.5 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, and/or 10 mg.

In some embodiments of the disclosure, control of the pH of the medium containing the therapeutic agent is required to maintain stability of the therapeutic agent for a desired period of time.

The desired pH of therapeutic agents of the disclosure can be set by titration of a solution of the therapeutic agent to a desired pH. In many instances, commercially available forms of a therapeutic agent are already formulated at an optimum pH for stability.

If a pH adjustment is required, the pH adjustment can be made inside reservoirs of the disclosure, by co-formulating the therapeutic agent with the appropriate additional ingredients. In other instances, it may be desirable to adjust the pH of the therapeutic agent before disposing it in the reservoir.

For the purpose of preparing full embodiments of the disclosure it may be advantageous to use a dry powder of the therapeutic agent that has been treated to produce the correct pH when hydrated. Such a dried powder may be prepared in any suitable preparation method, including drying or lyophilization of the therapeutic agent in solution. For the preparation of peptide and protein formulations lyophilization is often preferred.

The therapeutic agent can be administered by any means known to one of skill in the art. For example, the therapeutic agent can be administered via the implantable drug delivery system of the present disclosure. In some embodiments, the present disclosure provides a method of administering a therapeutic agent to a subject in need thereof, the method including implanting in the subject an implantable drug delivery system of the present disclosure containing a pharmaceutical composition of the present disclosure including the therapeutic agent and a polymeric buffering agent comprising a polymer functionalized with a plurality of acid groups or a plurality of base groups, wherein the therapeutic agent elutes from the implantable drug delivery system, thereby administering the therapeutic agent.

VII. Stabilizing Agents

Some embodiments of the disclosure include stabilizing agents in the form of polymers having a plurality of stabilizing groups. In some embodiments of the disclosure the stabilizing groups include pH sensitive groups, such as acidic groups, basic groups, or a combination thereof.

In some embodiments, a single type of pH sensitive group is present on the polymer, in some embodiments a variety of pH sensitive groups is present. In some embodiments, the pH sensitive groups are weakly acidic groups. In some embodiments, the weakly acidic groups are present on acrylic acid monomer residues or on methacrylic acid monomer residues, or on a combination of both.

In some embodiments of the disclosure, the polymeric stabilizing agent is present in essentially insoluble form.

In some embodiments the essentially insoluble form is obtained by incorporating cross-linkers into the polymer.

Some cross-linked polymeric stabilizing agents may be referred to as cross-linked polyacids. Well-known cross-linked polyacids include weakly acidic materials, such as cross-linked poly acrylic acid and strongly acidic materials, such as cross-linked polystyrene sulfonic acids, as well as weakly basic materials, such as cross-linked polyacrylate backbones with tertiary amine groups, and strongly basic materials, such as cross-linked polystyrene backbones with quaternary ammonium groups. These materials are often used as ion exchange resins (IER), and commercially available ion exchange resins are potentially suitable for use as stabilizing agents in the present disclosure.

In some embodiments of the disclosure, weakly acidic or weakly basic ion exchange resins (IER) are present. Weakly acidic or weakly basic ion exchange resins may be used advantageously by employing their capability to form buffer systems. Buffer systems are essentially mixtures of weak acids or weak bases with their respective conjugated bases or acids (salts). For instance, a weakly acidic buffer might contain a certain amount of an organic acid, like a carboxylic acid R—COOH, together with its conjugated base, like the sodium salt R—COO$^-$Na$^+$. Likewise, a weakly basic buffer might contain an amine R—NH$_2$, together with its conjugated acid, like the HCl salt R—NH$_3^+$ CL$^-$.

The pH of a buffer system is determined by the pKa of the acid and the ratio of the concentrations of the conjugated acid and conjugated base, as described in the Henderson-Hasselbalch equation:

$$pH = pK_a + \log\frac{[A^-]}{[HA]}$$

where [A$^-$] is the concentration of the conjugated base, and [HA$^+$] is the concentration of the conjugated acid. As a rule of thumb, the useable buffer range for a buffer system is between pH levels 2 units below the pKa of the acid in the formulation and 2 units above it. Preferred buffer ranges are between pH levels 1 unit below the pKa of the acid and 1 unit above it.

For example, a useable buffer range for acetic acid, with a pKa of about 4.7 is between about 2.7 and about 6.7. One buffer range is between about pH 3.7 and about 5.7.

The use of buffering crosslinked polymeric stabilizing agents may be particularly advantageous in combination with therapeutic agents that require a limited pH range to remain stable.

Examples of acidic groups of the disclosure include, but are not limited to, carboxylic acids, carbonic acids, sulfonic acids, sulfinic acids, sulfenic acids, phosphonic acids and phosphenic acids.

Examples of basic groups of the disclosure include, but are not limited to, primary, secondary, tertiary amines and quaternary ammonium groups.

In some embodiments the stabilizing groups are based on the so-called "Good buffers", developed by NE Good and his research team. These zwitterionic buffers meet most of the requirements that biological buffers have to fulfil.

Polymers of the disclosure may be present in variety of architectures, such as linear, branched, hyperbranched, star, dendritic, cross-linked, comb, etc.

Polymeric backbones of the disclosure include, but are not limited to, addition and condensation polymers.

Polymeric backbones may be homopolymers or copolymers. Copolymers include, but are not limited to, random copolymers and block copolymers.

Addition polymeric backbones include, but are not limited to polyolefines, polyvinyls, polyacrylates, polymethacrylates and polystyrenes.

Condensation polymers include, but are not limited to, polyesters, polyethers, polyamides, polyurethanes, polycarbonates, polyureas, polysulfides and polysiloxanes.

Crosslinking agents for addition polymers are well known in the art and include, but are not limited to a wide variety of di-functional olefins, such as divinyl benzene, ethylene glycol dimethacrylate and methylene bisacrylamide. Further lists of crosslinking agents are available in commonly accessible literature, such as commercial websites like the Sigma Aldrich website. https://www.sigmaaldrich.com/content/dam/sigma-aldrich/docs/Aldrich/Technical_Ads/al_ms_ad10_crslking_agents.pdf Crosslinking of condensation polymers is often achieved by including trifunctional or tetrafunctional monomeric analogs of the difunctional monomeric building blocks used for the linear polymer backbone.

In some embodiments of the disclosure, non-stabilizing monomers may be present in polymer chains of the polymeric stabilizing agents. For instance, in some embodiments of the disclosure acrylic monomers other than acidic or basic monomers may be present, such as methyl methacrylate or hydroxyethylmethacrylate monomers.

In some embodiments, a single type of polymer is present, in some embodiments, multiple types of polymers are present.

The use of crosslinked polymeric stabilizing agents may be particularly useful in combination with sustained release drug delivery devices that are designed to release their payload of therapeutic agent over an extended period of time in the body of a subject being treated with the therapeutic agent releasing device. Many therapeutic agents, including many peptides and proteins have molecular sizes that are significantly larger than those of commonly used buffering agents, which are often relatively low molecular weight agents, such as acetate, fumarate, citrate and other low molecular weight species. Because of their small size, such buffer systems often have higher mobility and transport rates than larger molecules such as peptides and proteins, and they tend to be released from sustained release therapeutic agent delivery devices faster than the agents they are designed to protect. Some embodiments of the disclosure include macromolecular polymeric buffering agents, like polyacids such as polyacrylic and polymethacrylic acids or combinations thereof.

Based on their molecular size, these macromolecules may not be able to cross a nanoporous membrane through the nanopores. In some instances, these soluble macromolecules may have a significant effect on the viscosity of the solution, which in some instances may not be desirable.

Some forms of these polyacids, like cross-linked forms, are essentially non-soluble and are substantially prevented or retarded from being released through the membranes.

Some cross-linked polymeric stabilizing agents used in the present disclosure are essentially supramolecular structures with a macroscopic size that blocks their release from the sustained release drug delivery device.

Crosslinked polymers of the disclosure can be used in an any desired physical form.

In some embodiments, cross-linked polymers may be present in particulate form, ranging from finely divided powders to coarse beads. The average particle size range may be from about 1 micrometer to up to any size that will fit inside a reservoir of the disclosure. In some instances, average particle size ranges of less than 1 micrometer may be present.

In some embodiments, the diameter of the particles may be from 1 micrometer to several millimeters, for instance up to 5 millimeters. In some instances, particles of more than 5 millimeter may be present. The particle size range and distribution may be determined based on the needs or preferences of a particular application. In some instances, a fine powder may be preferred and a particle size distribution roughly between 10 and 100 micrometers may be suitable. In other instances, beads may be preferred and a particle size roughly between 50 and 250 micrometers may be suitable.

For instance, particle sizes of embodiments of the disclosure may be from 1 to 10 micrometer, or from 1 to 100 micrometer, or from 1 to 1000 micrometer, or from 1 to 5000 micrometer, or from 10 to 100 micrometer or from 10 to 1000 micrometer or from 10 to 5000 micrometer, or from 100 to 1000 micrometer, or from 100 to 5000 micrometer, or from 1000 to 5000 micrometer, or from any size range in between 1 and 5000 micrometer.

Particle size ranges may be between 10 micrometer and 1 millimeter, and more preferred particle size ranges may be between 100 micrometer and 1 millimeter.

The particle shape may be regular, or semi-regular, like spherical or near-spherical particles, such as those obtained from a suspension polymerization process. In other instances, the particles may be irregular in shape, such as those resulting from a grinding process. In some instances, the polymers may be present in specific shapes, like cylinders, cubes, spheres, oblongs, and the like. In some instances, the shapes may be specifically tailored to the delivery device, for instance a polymer shaped into a cylinder to match the inner diameter of the reservoir of the device.

In some instances, mixtures of different physical shapes may be used.

In some embodiments, the polymers may be used in a porous configuration, in order to facilitate transport of molecules and ions throughout the bulk of the polymer.

In some embodiments, the polymers may be used in a dense or low-porosity configuration.

In some instances, the polymers, in hydrated form, may be relatively rigid. Typically, such polymers will have a high degree of cross-linking, like 5% (w/w) or more, to limit swelling during uptake of water. In some instances, the polymers, in hydrated form, may be soft and gel-like substances. Typically, such configurations will have low degrees of crosslinking, like 1% (w/w) or less. The exact desired degree of cross-linking may depend on several factors, including the hydrophilicity of the constituent monomers of the polymer, and may be determined experimentally.

Some embodiments, of the disclosure include polymeric stabilizing agents based on weakly acidic ion exchange resins (IER). Weakly acidic polymeric stabilizing agents may be particularly useful for the stabilization of therapeutic peptides and proteins. Many therapeutic peptides and proteins include asparagine residues which are particularly vulnerable to deamidation reactions converting the asparagine to aspartic acid. Glutamine residues have similar vulnerabilities albeit at lower reaction rates.

Deamidation reactions can be catalyzed by high or low pH, and in particular at pH levels above about 6.0 to about 6.5, depending on the specific peptide and protein, these reactions may proceed at rates that are unacceptable for the dosage form in which the therapeutic peptide or protein is formulated.

Figure 2:
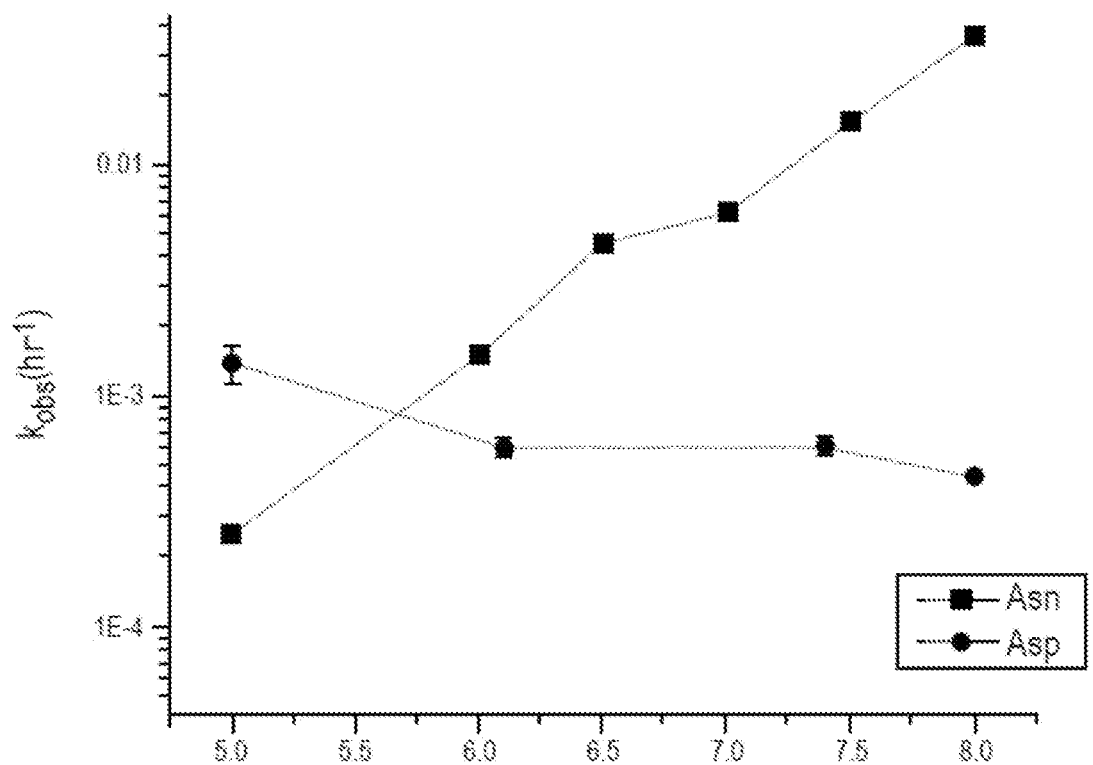
FIG. 2 represents a pH vs. stability profile of a model peptide.

As can be seen in FIG. 2, there may be a saddle point in the pH-driven degradation rates of peptides and proteins susceptible to deamidation at pH levels between about 5.0 and 6.0. One therapeutic agent of the disclosure, exenatide, has a rapidly decreasing stability half-life above pH 6.5.

Cross-linked poly-acrylic acid and poly-methacrylic acid have pKa levels in the range of 5.5 to 6.0, which puts their useable buffer range in a pH range between about 3.5 and 8.0, and their typically preferred pH buffer range in a pH range between about 4.5 and 7.0, making them highly suitable stabilizing agents for many peptides and proteins of this disclosure.

In the specific context of this disclosure, a buffer range of embodiments of the disclosure may be as low as 2 units below the pKa of the buffering agent. Since upon implantation in the body of the subject the physiological pH of the medium surrounding the implant will be close to about pH 7.4, proton exchange between a formulation in the reservoir of an implanted device and this physiological environment will tend to drive the internal pH of the formulation up. Providing a formulation at the lower end of the pH range of an incorporated buffer may provide additional buffer capacity, if so desired.

Additionally, acrylic acid and methacrylic acid are relatively small monomers, and therefore polymers and copolymers of these monomers carry a high density of acidic groups on a weight by weight basis, making them highly effective as stabilizing agents. In some embodiments, the cross-linked polymeric stabilizing agents are cross-linked poly-acrylic acid or poly-methacrylic acid, or mixtures thereof or copolymers of acrylic and methacrylic acid.

Crosslinked poly-acrylic acid and poly-methacrylic acid are used commercially as ion exchange resins. In some embodiments of the disclosure ion exchange resins are used as stabilizing agents. Potentially suitable ion exchange resins are produced by Mitsubishi Chemical Corporation under the name "Diaion" and by Purolite Corporation under the name "Purolite". In some instances, Diaion WK40L and Purolite 104plus and Purolite C115 may be suitable stabilizing agents for the stabilization of peptide and protein formulations. Others include Diaion WK10, Diaion WK11, Diaion WK100, and Diaion WT01S.

In certain instances, the amount of polymeric stabilizing agent is about 0.1% to about 25% w/w or up to 50% w/w of the formulation containing the therapeutic agent. In certain instances, the amount of polymeric stabilizing agent is about 0.1% to about 15% w/w, or up to 20% w/w; or about 1% to about 12% w/w; or about 2% to about 10% w/w; or about 5% to about 15% w/w, or about 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, and/or 15% w/w.

In certain instances, the amount of polymeric stabilizing agent in a reservoir is about 1.0 mg to 1000 mg, such as about 1 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, and/or 1000 mg. In certain instances, the amount of polymeric stabilizing agent is about 1.0 mg to 100 mg; or about 1.0 mg to 50 mg; or about 1.0 mg to 40 mg; or about 1.0 mg to 30 mg; or about 1.0 mg to 20 mg; or about 1.0 mg to 10 mg; or about 0.1 to about 15 mg such as approximately 0.5 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 10.5 mg, 11 mg, 11.5 mg, 12 mg, 12.5 mg 13 mg, 13.5 mg, 14 mg, 14.5 mg, 15 mg. In certain instances, 1-2 grams can be used.

In certain instances, the polymeric stabilizing agent is an insoluble polymer such as a solid that remains in the reservoir of the implantable device during operation. In certain instances, the polymeric stabilizing agent is an insoluble polymer that is not released during operation. In certain instances, the polymeric stabilizing agent is an insoluble polymer and forms a heterogeneous solid mixture with the therapeutic agent and the remaining formulation. In certain instances, the polymeric stabilizing agent does not form a hydrogel, xerogel or matrix for sustained release of the therapeutic agent. In certain instances, the polymeric stabilizing agent is a solid that remains in the reservoir of the implantable device.

In some embodiments of the disclosure, control of the pH of the stabilizing agent is required to maintain stability of the therapeutic agent for a desired period of time. The desired pH of polymeric stabilizing agents of the disclosure can be set by titration of a quantity of the stabilizing agents, in the case of a cross-linked polymeric acid by titration with a base, such as NaOH. Titration of polymeric acids is well-known in the art, and titration of stabilizing agents of the disclosure can be achieved by stirring a suspension of particulates of a cross-linked polymeric acid with an appropriate strength of a base like NaOH until equilibration at a desired pH level has been achieved. Background for experimental procedures with stabilizing agents in the form of ion exchange resins can be found in readily available literature, such as text books. E.g. Ion Exchange, F. Hellfferich, Dover Publications Inc. New York, 1995, P. 81-94). pH adjustments of Purolite PPC104 plus are shown in the Table in Example 19.

The pH adjustment can be made inside reservoirs of the disclosure by co-formulating the stabilizing agents with the appropriate additional ingredients. In other instances, it may be desirable to adjust the pH of the stabilizing agent before disposing it in the reservoir.

In some embodiments, it may be preferred to use a dry powder or dry beads of a polymeric stabilizing agent that has been treated in advance to produce the correct pH when hydrated. Such dry powder or beads may be prepared by incubating a known amount of the powder or beads with an appropriate amount of base, and then filtering and drying the powder or beads.

Some embodiments include a step of partially neutralizing pH sensitive groups of the stabilizing agent to an extent that upon hydration of the cross-linked polymeric stabilizing agent and in the presence of the therapeutic agent in the reservoir with an aqueous solvent a formulation develops with a predetermined pH. In some embodiments, the pH is between about 3.5 and about 7, such as 3.5, 4.0, 4.5, 5.0, 6.0, 6.5, 7.0 or 7.5. In some embodiments, the aqueous solvent is interstitial fluid of a subject into which the device has been implanted.

All of the above examples of polymeric stabilizing agents and their compositional components may be used in embodiments of the disclosure, and those with ordinary skills in the art of polymer chemistry will be able to identify and select a suitable crosslinked polymeric stabilizing agent for the intended purpose of an embodiment of the disclosure.

VIII. Formulations

Some embodiments of the disclosure include formulations of therapeutic agents.

In one embodiment, the disclosure provides a therapeutic formulation, the formulation comprising:

therapeutic agent; and a polymeric stabilizing agent comprising an insoluble polymer having a plurality of pH sensitive stabilizing groups, which is a member selected from the group consisting of a cross-linked poly-acrylic acid, a cross-linked polymethacrylic acid, or mixtures thereof or copolymers of acrylic and methacrylic acid.

In some instances, the pH sensitive stabilizing groups are neutralized to an extent that upon hydration of the therapeutic agent and the stabilizing agent with an aqueous medium having a neutral pH a fluid develops with a pH between 3.5 and 7.5.

In some instances, the pH sensitive stabilizing groups are neutralized to an extent that upon hydration of the therapeutic agent and the stabilizing agent with an aqueous medium having a neutral pH a fluid develops with a pH between 3.5 and 7.5 such as about 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, and/or 7.5.

Some embodiments of the disclosure include formulations of therapeutic agents with polymeric stabilizing agents.

Any of the therapeutic agents in this disclosure may be combined with any of the stabilizing agents in this disclosure, as appropriate, and as can be determined by one of ordinary skills in the art of therapeutic agent stabilization.

In some embodiments of the disclosure, formulations of the therapeutic agent may be combined with devices of the disclosure, in which the devices include a capsule configured for implantation, a reservoir, and a nanoporous membrane with a plurality of pores. The membrane is attached to the capsule in fluid contact with the reservoir and provides a pathway for the therapeutic agent out of the reservoir.

Some formulations of the disclosure include a peptide or protein and a polyacid at a pH between about 5.0 and about 6.0. In some formulations, the peptide is an incretin mimetic. In some formulations the incretin mimetic is exenatide. In some embodiments, the polyacid is polyacrylic acid or polymethacrylic acid. In some embodiments, the polymeric stabilizing agent is Purolite 104+ or Purolite C115, or Purlite C104Plus or an analog thereof.

Some formulations of the disclosure include a water soluble salt. Various salts include, but are not limited to, sodium chloride, potassium chloride, calcium chloride, magnesium chloride, sodium acetate, and sodium citrate. In some embodiments, the water soluble salt may be at a concentration of about 1 mM to 1M; or 10 mM to 500 mM; or about 70 mM to about 200 mM; or about 100 mM to about 170 mM; or about 140 mM to about 160 mM. In some instances, the water soluble salt may be sodium chloride at 154 mM. In some instances, a salt concentration is below 1 mM or above 1M may be present.

In certain instances, the reservoir contains about 5 to about 20 milligrams of a cross-linked form of methacrylic acid as the stabilizing agent and about 20 to about 60 microliter of an aqueous solution of between 10%-50% (w/w) exenatide as the therapeutic agent, at a pH between 4.0 and 7.0 and NaCl.

In certain instances, the reservoir contains about 5 to about 20 milligrams of a cross-linked form of poly-acrylic acid as the stabilizing agent and about 20 to about 60 microliter of an aqueous solution of between 10%-50% (w/w) exenatide as the therapeutic agent, at a pH between 4.0 and 7.0 and NaCl.

In certain instances, the reservoir contains about 5 to about 20 milligrams of a cross-linked form of poly-acrylic acid and cross-linked poly-methacrylic acid as the stabilizing agent and about 20 to about 60 microliter of an aqueous solution of between 10%-50% (w/w) exenatide as the therapeutic agent, at a pH between 4.0 and 7.0 and NaCl.

In certain instances, the reservoir contains about 5 to about 20 milligrams of a cross-linked form of copolymers of acrylic acid and methacrylic acid as the stabilizing agent and about 20 to about 60 microliter of an aqueous solution of between 10%-50% (w/w) exenatide as the therapeutic agent, at a pH between 4.0 and 7.0 and NaCl.

Formulations of the disclosure may include the therapeutic agent in any desirable form, including solid forms, as well as fluid forms, such as solutions, suspensions, emulsions, colloids and dispersions. In some embodiments of the disclosure, therapeutic agents can be present in complexated form with polymeric stabilizers, for instance by complexation of a positively charged therapeutic agent with a negatively charged stabilizing agent.

Formulations of the disclosure may additionally include pharmaceutically acceptable inactive ingredients, such as buffering agents, solubility modifiers, surfactants, soluble high and low molecular weight stabilizers, anti-oxidants, antimicrobials and the like. A list of potentially suitable inactive ingredients used in currently marketed pharmaceutical products in the US can be found on the website of the United States Food and Drug Administration (FDA).

Formulations of the disclosure may include any of the therapeutic agents in disclosure, and, if desired, any of the polymeric stabilizing agents in this disclosure.

Some embodiments of the disclosure provide methods for the preparation of formulations of one or more therapeutic agents. In some embodiments, the formulations include a polymeric stabilizing agent. Some embodiments of the disclosure include methods for the preparation of suitably pH adjusted formulations containing polymeric stabilizing agents and therapeutic agents.

Polymeric stabilizing agents and therapeutic agents of the disclosure may be combined in any desired method into formulations of the disclosure. Resulting formulations may have any desired physical state, including dry powder formulations and suspensions of the polymeric stabilizing agent in a fluid formulation of the therapeutic agent. Suitable fluid formulations include solutions, suspensions, emulsion, colloids and dispersions.

The therapeutic agent and the polymeric stabilizing agent may be combined as dry powders, after which a liquid vehicle is added, or one or both components may be taken up in a liquid vehicle before combining them together.

For formulations intended for parenteral use, it is often desired to provide the formulation in a state resembling physiological conditions and in some embodiments adjustments of the sodium chloride concentration to physiological levels (154 mM) may be preferred.

IX. Stabilization Methods

Some methods of the disclosure provide stabilization of a therapeutic agent by combining the therapeutic agent with a stabilizing agent, in which the stabilizing agent is a polymeric agent having stabilizing groups. In some embodiments, the stabilizing agent is an insoluble polymeric agent. In some embodiments, the insoluble polymeric agent is a cross-linked polymeric agent. In some embodiments, the stabilizing groups are pH sensitive groups. In some embodiments, the pH sensitive groups are weakly acidic groups. In some embodiments, the weakly acidic groups are present on acrylic acid monomer residues or on methacrylic acid monomer residues, or on a combination of both.

In some embodiments of the disclosure the combined therapeutic agent and stabilizing agent are disposed within a reservoir of a capsule of a device for sustained release of the therapeutic agent, wherein the capsule is configured for implantation. The capsule has at least one nanoporous membrane, such as the titania nanotube membranes described in U.S. Pat. No. 9,814,867, providing a diffusion path for the therapeutic agent out of the reservoir. The dimensions of the stabilizing agent are larger than the pore size of the membrane, thereby substantially preventing release of the stabilizing agent from the reservoir.

In some embodiments of the disclosure the stabilizing agent is used as a buffer system, maintaining the pH of a fluid form of the therapeutic agent in the reservoir within a desired range. In some preferred embodiments, the pH range is between about 3.5 and about 7.5. In some embodiments, the pH range is between about 5.0 and about 6.0.

Some methods of the disclosure include a partial pre-neutralization of the pH sensitive groups on the stabilizing agent and then drying the partially neutralized stabilizing agents, such that upon hydration of the stabilizing agent a fluid develops with a pH within a desired range. In some methods of the disclosure the hydrating fluid includes the therapeutic agent. In some methods of the disclosure the hydration is performed inside the reservoir of the capsule. In some methods of the disclosure the hydration is performed outside the capsule and filling of the capsule is performed with the fluid combining the therapeutic agent and the stabilizing agent.

Methods of the disclosure may be particularly useful for the stabilization of peptides and proteins. Many peptides and proteins have optimal stability in a pH range between about 3.5 and about 7.5. Some peptides and proteins have optimal stability in a pH range between about 5.0 and about 6.0.

In some embodiments of the disclosure, the therapeutic agent is a peptide or protein. In some embodiments, the therapeutic agent is an incretin mimetic. In some embodiments, the incretin mimetic is exenatide.

Upon implantation of the device in the body of a subject mass transport of the therapeutic agent together with low molecular weight ionized species out of the reservoir occurs, resulting in a net transport of protons out of the reservoir. The resulting increase in pH is counteracted by increased levels of ionization of the stabilizing groups on the polymer, resulting in a reduction in the rate of pH increase.

X. Treatment Methods

Some embodiments of the disclosure provide methods of treating a disease or condition in subjects using devices and formulations of the disclosure. Subjects include human and veterinary subjects. The methods include providing a device of the disclosure including a therapeutic agent and a stabilizing agent and implanting the device in the subject, thereby treating the disease or condition.

Any suitable therapeutic agent and polymer can be used in the method of the present disclosure, as described above. In some embodiments, the therapeutic agent can be exenatide.

Any suitable type of diabetes can be treated using the method of the present disclosure. The term diabetes encompasses several different hyperglycemic indications. These states include Type 1 (insulin-dependent diabetes mellitus or IDDM) and Type 2 (non-insulin dependent diabetes mellitus or NIDDM) diabetes. The hyperglycemia present in individuals with Type 1 diabetes is associated with deficient, reduced, or nonexistent levels of insulin which are insufficient to maintain blood glucose levels within the physiological range. Methods of treatment of Type 1 diabetes involves administration of replacement doses of insulin, generally by a parenteral route.

The hyperglycemia present in individuals with Type 2 diabetes is initially associated with normal or elevated levels of insulin; however, these individuals are unable to maintain metabolic homeostasis due to a state of insulin resistance in peripheral tissues and liver and, as the disease advances, due to a progressive deterioration of the pancreatic (3-cells which are responsible for the secretion of insulin. In some embodiments, the diabetes can be type 2 diabetes. In some embodiments, the diabetes can be type 1 diabetes. In some embodiments, the disease can be type 2 diabetes. In some embodiments, the disease can be type 1 diabetes.

In certain aspects, suitable daily dosage ranges for the therapeutics of the present disclosure include from about 0.1 μg to about 10,000 or about 1 μg to about 1000 or about 10 μg to about 750 or about 25 μg to about 500 or about 50 μg to about 250 μg. Suitable daily dosages for the compound of the present disclosure include about 1 μg, 5, 10, 20, 30, 40, 50, 60, 70, 80, 90, 100, 200, 300, 400, 500, 600, 700, 800, 900 or 1000 μg.

In certain instances, the disclosure provides a method of treating diabetes (e.g., to a method lowering blood glucose levels, or to a method of improving glycemic control) by administering a GLP-1 analogue such as, for example, exenatide using an implantable device, the GLP-1 analogue is administered in an effective daily dose of about 1 μg to about 100 or 10 μg to about 100 or about 10 μg to about 50 μg (e.g., the implantable device provides release of the GLP-1 analogue at a range of about 10 μg to about 100 μg GLP-1 analogue each day, or about 10 μg to about 50 μg per day).

The doses suitable for the treatment of diabetes can provide any suitable mean steady-state plasma concentration of the therapeutic agent in the subject. For example, the mean steady state plasma concentration can be from 10 pg/ml to 10,000 ng/ml. In some embodiments, the mean steady state plasma concentration for exenatide can be from 170 pg/ml to 600 pg/ml. In some embodiments, the mean steady state plasma concentration for exenatide can be from 170 pg/ml to 350 pg/ml. In some embodiments, the mean steady state plasma concentration for exenatide can be from 170 pg/ml to 290 pg/ml.

In certain embodiments, the exenatide concentration is sufficient to achieve an average or minimum circulating blood plasma level of exenatide of at least about 50 pg/ml for a period of at least about 12 hours, at least about 1 day, at least about 2 days, at least about 3 days, at least about 1 week, at least about 2 weeks, at least about 3 weeks, at least about 1 month, at least about 3 months, or at least about 6 months or even more such as 1 year.

The implantation can be performed by any means known to one of skill in the art, for instance through subcutaneous insertion of the device using a hollow need The present disclosure provides a method of treating a disease by administering a therapeutic agent suitable to treat the disease from an implantable drug delivery system of the present disclosure using a composition of the present disclosure. The present disclosure provides a method of treating diabetes by administering a therapeutic agent from an implantable drug delivery system of the present disclosure using a composition of the present disclosure. In some embodiments, the present disclosure provides a method of treating diabetes in a subject in need thereof, the method including administering to the subject a therapeutically effective amount of a therapeutic agent via an implantable drug delivery system of the present disclosure containing a pharmaceutical composition of the present disclosure including the therapeutic agent and a polymer functionalized with a plurality of stabilizing groups, thereby treating the diabetes. In some embodiments, the present disclosure provides a method of treating diabetes in a subject in need thereof, the method including administering to the subject a therapeutically effective amount of a therapeutic agent via an implantable drug delivery system of the present disclosure containing a pharmaceutical composition of the present disclosure including the therapeutic agent and a polymer functionalized with a plurality of acid groups or a plurality of base groups, wherein the acid and base groups are not all neutralized during the administering, thereby treating the diabetes.

Any suitable disease can be treated by the method of the present disclosure. For example, the disease can be diabetes, cancer, neurological disorders, inflammatory diseases, and others. In some embodiments, the disease can be diabetes.

Any suitable therapeutic agent and polymer can be used in the method of the present disclosure, as described above. In some embodiments, the therapeutic agent can be exenatide.

Any suitable type of diabetes can be treated using the method of the present disclosure.

The term diabetes encompasses several different hyperglycemic indications. These states include Type 1 (insulin-dependent diabetes mellitus or IDDM) and Type 2 (non-insulin dependent diabetes mellitus or NIDDM) diabetes. The hyperglycemia present in individuals with Type 1 diabetes is associated with deficient, reduced, or nonexistent levels of insulin which are insufficient to maintain blood glucose levels within the physiological range. Methods of treatment of Type 1 diabetes involves administration of replacement doses of insulin, generally by a parenteral route.

The hyperglycemia present in individuals with Type 2 diabetes is initially associated with normal or elevated levels of insulin; however, these individuals are unable to maintain metabolic homeostasis due to a state of insulin resistance in peripheral tissues and liver and, as the disease advances, due to a progressive deterioration of the pancreatic (3-cells which are responsible for the secretion of insulin. In some embodiments, the diabetes can be type 2 diabetes. In some embodiments, the diabetes can be type 1 diabetes. In some embodiments, the disease can be type 2 diabetes. In some embodiments, the disease can be type 1 diabetes.

Any suitable subject can be treated using the method of the present disclosure. In some embodiments, the subject can be a human.

The therapeutic agent can be delivered in any therapeutically effective amount. The therapeutic agent of the present disclosure can be delivered in any suitable amount, and can depend on various factors including, but not limited to, weight and age of the subject, state of the disease, etc. Suitable dosage ranges for the compound of the present disclosure include from about 0.1 µg to about 10,000 or about 1 µg to about 1000 or about 10 µg to about 750 or about 25 µg to about 500 or about 50 µg to about 250 µg. Suitable dosages for the compound of the present disclosure include about 1 µm, 5, 10, 20, 30, 40, 50, 60, 70, 80, 90, 100, 200, 300, 400, 500, 600, 700, 800, 900 or 1000 µg.

The doses suitable for the treatment of diabetes can provide any suitable mean steady-state plasma concentration of the therapeutic agent in the subject. For example, the mean steady state plasma concentration can be from 10 pg/ml to 10,000 ng/ml. In some embodiments, the mean steady state plasma concentration for exenatide can be from 170 pg/ml to 600 pg/ml. In some embodiments, the mean steady state plasma concentration for exenatide can be from 170 pg/ml to 350 pg/ml. In some embodiments, the mean steady state plasma concentration for exenatide can be from 170 pg/ml to 290 pg/ml.

In certain embodiments, the exenatide concentration is sufficient to achieve an average or minimum circulating blood plasma level of exenatide of at least about 50 pg/ml for a period of at least about 12 hours, at least about 1 day, at least about 2 days, at least about 3 days, at least about 1 week, at least about 2 weeks, at least about 3 weeks, at least about 1 month, at least about 3 months, or at least about 6 months or even more.

XI. Examples

Below are examples of substances based on a Poly-Amido-Amine dendritic backbone structure, that are suitable for use in formulations of the disclosure.

1. PAMAM-NH$_2$ (PAMAM)
2. PAMAM-COOH (PAMAM carboxylic acid)
3. PAMAM-NH—CO—CH$_2$—CH$_2$—COOH (PAMAM succinic acid)
4. PAMAM-CO—NH—CH$_2$—CH$_2$—OH (PAMAM amidoethanol)
5. PAMAM-Tocopherol
6. PAMAM-Retinol
7. PAMAM-BHT
8. PAMAM-Methionine
9. PAMAM-Maltose
10. PAMAM-Silver Sulfadiazine
11. PAMAM-hexachlorophene
12. PAMAM-Streptomycin Polymers 1, 2, 3 and 4 are commercially available, for instance from Dendritech, Inc. in Midland, Michigan. Polymer 5 can be prepared by esterification of Polymer 2 with the phenyl hydroxyl group of tocopherol. Polymer 6 can be prepared by esterification of Polymer 3 with the terminal hydroxyl group of retinol. Polymer 7 can be prepared by esterification of Polymer 2 with the phenyl hydroxyl group of BHT. Preparation of Polymer 6 and Polymer 7 can proceed via Fischer esterification under conditions of water removal, for instance with molecular sieves or under azeotropic distillation, with catalytic amounts of an acid like p-toluenesulfonic acid. Polymer 8 can be prepared by amide bond formation between the COOH group of methionine with the NH$_2$ group from Polymer 1, such as by using a carbodiimide reagent. Polymer 9 can be prepared by formation of a Schiff's base between the aldehyde form of maltose and the NH$_2$ group from Polymer 1, followed by a reduction with sodium borohydride. Polymer 10 can be prepared similarly to Polymer 8, by reacting the phenyl NH$_2$ group of silver sulfadiazine with the COOH group of Polymer 3. Polymer 11 can be prepared similarly to Polymer 6, by esterification of the phenyl hydroxy of hexachlorophene with the acid group of Polymer 2. Polymer 12 can also be prepared via esterification similarly to Polymer 6, such as by reaction of Polymer 2 or Polymer 3 with a hydroxy on the streptomycin molecule, or by preparing an amide under conditions similar for preparation of Polymer 8.

Active agents include the following:

Exenatide, a peptide molecule, is sensitive to oxidation, as well as to degradation at pH levels above 6.

Octreotide, a peptide molecule, is sensitive to oxidation and is preferably kept at a pH between 4 and 4.5.

Fluphenazine is a low molecular weight anti-psychotic with a phenothiazine group that is prone to oxidation. It has limited water solubility.

Example 1

Composition

Exenatide, 10 µg, is admixed with 10 mg of a Generation 5 PAMAM dendrimer with sodium carboxylate end groups and an ethylenediamine core.

Example 2

Treating Diabetes

A 50 year-old male, weighing 175 pounds, presents to a physician with type 2 diabetes. The physician implants in the patient the drug delivery system described above containing exenatide and a Generation 5 PAMAM dendrimer with sodium carboxylate end groups and an ethylenediamine core.

Example 3

Preparation of Aqueous Formulation of PAMAM-COOH, PAMAM-Methionine and Exenatide An aqueous formulation is prepared by co-dissolving 4 grams of exenatide, 2 grams of Polymer 2 and 0.5 grams of Polymer 8 in water for injection and bringing the total volume to 10 ml.

The estimated hydrodynamic diameter of exenatide is about 2.4 nm. In order to achieve a constant release rate, the solution is used in combination with a nanopore membrane-controlled drug delivery system with a pore size of 7 nm.

Polymers 2 and 8, based on a $6^{th}$ generation PAMAM have a hydrodynamic radius larger than 7 nm, based on the presence of the carboxylic acid and methionine groups on the PAMAM backbone and will be substantially retained in the drug delivery system during the implantation period.

Example 4

Anti-Microbial Aqueous Formulation of PAMAM-COOH, PAMAM-Methionine, PAMAM-Silver Sulfadiazine and Exenatide The formulation of Example 3 is prepared with the addition of 20 mg of Polymer 10.

Example 5

Solid Formulation of PAMAM-COOH, PAMAM-Tocopherol and Exenatide

A powder mix is prepared of 5 parts exenatide, 5 parts of Polymer 2, and 1 part of Polymer 5. The powder mix can be prepared in any pharmaceutically suitable type of powder mixer. The powder can be filled directly into a reservoir of a drug delivery system, or can be compressed into a pellet and loaded as such in the reservoir.

Example 6

Anti-Microbial Solid Formulation of PAMAM-COOH, PAMAM-Tocopherol, PAMAM-Silver Sulfadiazine and Exenatide The formulation of Example 5 is prepared with the addition of 0.5 parts of Polymer 10.

Example 7

Suspension Formulation of PAMAM-COOH, PAMAM-Tocopherol and Exenatide

A suspension formulation can be prepared by suspending the formulation of Example 5 or Example 6 in 11 parts of pharmaceutical grade vegetable oil.

Example 8

Aqueous Formulation of PAMAM-COOH, PAMAM-Methionine and Octreotide

An aqueous formulation is prepared by co-dissolving 2 parts of octreotide, 1 part of Polymer 2 and 0.1 part of Polymer 8 in water for injection for a solution with a solid content of 40% w/w.

The estimated hydrodynamic diameter of octreotide is about 1.6 nm. In order to achieve a constant release rate, the solution is used in combination with a nanopore membrane-controlled drug delivery system with a pore size of 5 nm. Polymers 2 and 8, based on a $4^{th}$ generation PAMAM, have a hydrodynamic radius larger than 5 nm, based on the presence of the carboxylic acid and methionine groups on the PAMAM backbone and will be substantially retained in the drug delivery system during the implantation period.

Example 9

Anti-Microbial Aqueous Formulation of PAMAM-COOH, PAMAM-Methionine, PAMAM-hexachlorophene and Octreotide The formulation of Example 8 is prepared with the addition of 20 mg of Polymer 11.

Example 10

Solid Formulation of PAMAM-COOH, PAMAM-Retinol and Octreotide

A powder mix is prepared of equal parts of octreotide and Polymer 2, with the addition of ⅕ part of Polymer 6. The powder mix can be prepared in any pharmaceutically suitable type of powder mixer. The powder can be filled directly into a reservoir of a drug delivery system, or can be compressed into a pellet and loaded as such in the reservoir.

Example 11

Anti-Microbial Solid Formulation of PAMAM-COOH, PAMAM-Retinol, PAMAM-Silver Sulfadiazine and Octreotide The formulation of Example 10 is prepared with the addition of 0.5 parts of Polymer 10.

Example 12

Suspension Formulation of PAMAM-COOH, PAMAM-Retinol and Octreotide

A suspension formulation is prepared by suspending the formulation of Example 10 or Example 11 in 2 parts of pharmaceutical grade vegetable oil.

Example 13

Solid Formulation of PAMAM-Tocopherol and Fluphenazine

A powder mix is prepared of 9 parts fluphenazine and 1 part Polymer 5. The powder mix can be prepared in any pharmaceutically suitable type of powder mixer. The powder can be filled directly into a reservoir of a drug delivery system, or can be compressed into a pellet and loaded as such in the reservoir.

The estimated hydrodynamic diameter of fluphenazine is about 1.4 nm. In order to achieve a constant release rate, the solution is used in combination with a nanopore membrane-controlled drug delivery system with a pore size of 4 nm. Polymer 5, based on a third generation PAMAM has a hydrodynamic radius larger than 4 nm, based on the presence of the tocopherol groups on the PAMAM backbone and will be substantially retained in the drug delivery system during the implantation period.

Example 14

Calculation of Diffusion Rate

According to Fick's Law, Flux F can be expressed as:

$$F = A \times D \times \Delta C \times 1/d$$

wherein
A = Total surface area for diffusion ($cm^2$)
D = Diffusion Coefficient ($cm^2/sec$)
$\Delta C$ = Concentration differential ($mg/cm^3$)
d = diffusion path length (cm)
Total surface area for diffusion A is calculated as $$A = N \times \pi \times r^2$$

wherein N = total number of nanopores and r is the radius of the nanopores.

In restricted diffusion through nanopores of appropriate diameter, the dependence of the rate of diffusion on concentration differential disappears, and, instead, the rate of diffusion becomes dependent on the pore diameter. The pore diameter can be controlled by the atomic layer deposition technique described in PCT Publication No. WO 2015/112811, the entirety of which is incorporated herein by reference.

The product of D, ΔC and ($\pi \times r^2$) can be rewritten as a permeation rate P, in this case with a dimension of mass over time, and unit of mg/sec. The permeation rate P can easily be determined in a traditional membrane-controlled diffusion cell experiment. Consequently, at a fixed nanopore length, the total flux F can now simply and entirely be controlled by the number of nanopores, N.

Diffusion Rate for Exenatide

In one example, for exenatide a delivery rate of 60 μg/day may be desired. In a diffusion cell experiment as mentioned above, a constant release rate profile is measured when using pores of 7 nm, at a rate of $4.5 \times 10^{-12}$ μg/second per nanopore, or $4 \times 10^{-7}$ μg/day per nanopore. In this case, a device with about $1.50 \times 10^8$ nanopores would be sufficient. At a pore density of $3 \times 10^8$ pores/mm$^2$, a window of open nanopores of about 0.5 mm$^2$ will meet the desired release rate profile.

In this example, for a device with a six-month duration of release rate and an efficiency of release of 80%, a payload of about 13 mg exenatide will be adequate. At a packing efficiency of 400 μg of exenatide per microliter of the reservoir of the device, a reservoir of 32.5 microliter will be required. For this application, a device can be designed with an internal reservoir of 2 mm diameter and 11 mm in length. The diameter of 2 mm will accommodate endcaps holding a membrane with an open window area of 0.5 mm$^2$ for the nanopores.

The final formulation in this device would be 13 mg of exenatide, 6.5 mg of Polymer 2, 2.6 mg of Polymer 8 and the remainder water for injection.

Diffusion Rate for Octreotide

In another example, a delivery rate of 160 μg/day may be desired for octreotide. In a diffusion cell experiment as mentioned above, a constant release rate profile is achieved with pores of 5 nm, at a rate of $9 \times 10^{-12}$ μg/second per nanopore, or $8 \times 10^{-7}$ μg/day per nanopore. In this case, a device with about $2 \times 10^8$ nanopores will be sufficient. At a pore density of $3.5 \times 10^8$ pores/mm$^2$, a window of open nanopores of about 0.6 mm$^2$ will meet the desired release rate profile.

In this example, for a device with a 3-month duration of release rate and an efficiency of release of 80%, a payload of about 17.5 mg octreotide will be adequate. With addition of 17.5 mg of Polymer 2, and about 3.5 mg of Polymer 6, a powder mix of 38.5 mg is obtained. At a powder packing efficiency of 85%, and assuming a powder density of 1.2 g/cm$^3$, a reservoir of 37 microliter will be sufficient.

For this application, a device can be designed with an internal reservoir of 2 mm diameter and 12 mm in length. The diameter of 2 mm will accommodate endcaps holding a membrane with an open window area of 0.6 mm$^2$ for the nanopores.

Diffusion Rate for Fluphenazine

In yet another example, for fluphenazine a delivery rate of 2500 μg/day may be desired. In a diffusion cell experiment as mentioned above, a constant release rate profile is achieved with pores of 4 nm, at a rate of $15 \times 10^{-12}$ μg/second per nanopore, or $1.3 \times 10^{-6}$ μg/day per nanopore. In this case, a device with about $2 \times 10^9$ nanopores will be sufficient. At a pore density of $3.5 \times 10^8$ pores/mm$^2$, a window of open nanopores of about 6 mm$^2$ will meet the desired release rate profile.

In this example, for a device with a 1-month duration of release rate and an efficiency of release of 80%, a payload of about 90 mg fluphenazine will be adequate. Using a powder mix of 9 parts fluphenazine and 1 part Polymer 5, a payload of 100 mg will be required.

At a powder packing efficiency of 85%, and assuming a powder density of 1.2 g/cm$^3$, a reservoir of about 100 microliter will be required. For this application, a device can be designed with an internal reservoir of 3 mm diameter and 15 mm in length. The diameter of 3 mm will accommodate endcaps with the required surface area for the nanopore membranes if both endcaps are used to hold a membrane.

Example 15

Compositions of PAMAM-COOH and Exenatide

The stabilizing capability of dendrimers with acidic end groups in a drug delivery system with a size cut-off membrane was demonstrated with the following example.

Cylindrical titanium reservoirs with an internal volume of 140 microliter were filled with a solution of pure exenatide or with a solution of exenatide with PAMAM-COOH.

The pure exenatide solution contained 20% exenatide in a citrate buffer of pH 4.9. The exenatide solution with PAMAM-COOH was prepared in a similar manner, with the addition of 20% (w/w) PAMAM-COOH. The final pH after addition of the PAMAM-COOH was between 3 and 4.

Both solutions contained 0.02% NaN$_3$ to prevent bacterial growth. The reservoirs were capped with a screw cap holding a dialysis membrane to allow for free exchange of small molecules and ions like protons and citrate buffer between the reservoirs and the incubation liquid, but to retain the PAMAM-COOH in the reservoirs.

The reservoirs were then incubated in phosphate-buffered saline (PBS) at pH 7.4 for 3 months. At the 3 month time point the solutions were analyzed by reverse phase high performance liquid chromatography (RP-HPLC).

The purity of the exenatide in the PAMAM-COOH solutions was still 100% of the initial value by RP-HPLC, while the purity on the exenatide-only solutions had dropped to 83%.

The following calculation demonstrates the use of PAMAM-COOH as a stabilizer in a formulation inside a drug delivery system with a nanoporous membrane having a nominal pore size of 6 nm. In this case, use of a 6$^{th}$ generation PAMAM-COOH stabilizer, with a diameter of 6.7 nm, will largely prevent release of the stabilizer through the pores. It should be noted that some escape of the PAMAM-COOH may occur, due to the fact that the pores in the membrane will have a pore size distribution around the nominal pore size of 6 nm.

In order to maintain charge neutrality, the loss of a proton needs to be compensated by uptake of another cation, in an environment of actual use most likely a sodium ion. Consequently, the loss of a proton essentially represents the neutralization of an acid group on a polymer. The effects of sodium ion transport have not been taken into account in this example.

Using Fick's Law for the calculation of Flux F, described above, calculation shows the rate of diffusion of acidic protons out of a device under the following conditions:

Calculation of total surface area for diffusion, A. The drug delivery system in this example has a membrane with 132 million nanotubes with a diameter of 6 nm, or $6 \times 10^{-7}$ cm. Accordingly, the total surface area for diffusion can be calculated as:

$$A = 132 \times 10^6 \times \pi \times (3 \times 10^{-7})^2 = 4 \times 10^{-5} \text{ cm}^2$$

Calculation of concentration differential, $\Delta C$. When using as internal pH of 4, and an external pH of 7, the concentration differential can be written as:

$$\Delta C = (10^{-1} \text{ mmole/cm}^3 - 10^{-7} \text{ mmole/cm}^3) = \sim 10^{-4} \text{ mmole/cm}^3$$

Proton diffusion coefficient, D, is $10^{-4}$ cm$^2$/sec, based on literature data.

Diffusion path length, d, is the nanotube length, which can be 50 micrometer, $50 \times 10^{-4}$ cm.

Based on the above, and on the assumption of strictly Fickian diffusion control, the loss rate of protons through the membrane is $8 \times 10^{11}$ mmole/second, equivalent to $7 \times 10^{-6}$ mmole/day.

In the case of PAMAM-COOH, there are 256 end groups on a 6th generation PAMAM backbone of 58,025 Da, so a weight equivalence of about 226 Da per acid group. Consequently, the rate of proton loss is equivalent to the loss of $7 \times 10^{-6} \times 226$ mg, or about 1.6 micrograms of PAMAM-COOH acid carrying capacity per day.

Example 16

Determination of Exenatide Purity

The following example provides a procedure for determining the purity of exenatide released by an implantable drug delivery system of the present disclosure.

Exenatide purity can be determined using HPLC under the following conditions:
HPLC Mobile Phase:
  Mobile Phase A (0.1% TFA in Water):
  Add 1 mL of trifluoroacetic acid to 1 L of water.
  Mobile Phase B (0.1% TFA in Acetonitrile):
  Add 1 mL of trifluoroacetic acid to 1 L of acetonitrile.
Standards:
  Exenatide Stock Solution (1.0 mg/mL):
  Add 1.40 mg of Exenatide to 1400 µL of water
  Standard 7 (100 µg/mL):
  Add 200 µL of Exenatide stock solution (1.0 mg/mL) to 1800 µL of water.
  Make a serial dilution of Standard 7 (100 µg/mL) with water to 0.5, 1, 2.5, 5, 10, 50, and 100 µg/mL.

| Table of HPLC Conditions | | |
|---|---|---|
| Column | Vydac, Protein C4, 3.2 mm xl 50 mm, 5 µm | |
| Mobile Phase A | 0.1% TFA in Water | |
| Mobile Phase B | 0.1% TFA in Acetonitrile | |
| Column Temperature | Ambient | |
| Autosampler Temperature | 4° C. | |
| Flow rate | 0.75 mL/min | |
| Injection volume | 25 µL | |
| Detector wavelength | 220 nm | |
| Gradient | Time (min) | Mobile Phase B (%) |
| | 0 | 25 |
| | 20 | 60 |
| | 20.1 | 25 |
| | 28 | 25 |
| Run time | 28 minutes | |

Example 17

Therapeutic agent: Exenatide acetate (Bachem Holding AG, Switzerland).

Stabilizing agent: Diaion WK40L (Mitsubishi Chemical Corporation, Japan).

Membranes were developed based on the process as described in U.S. Pat. No. 9,814,867.

50 microliter polycarbonate capsules and titanium screw caps to attach the membrane to the capsule were prepared by commonly available machining methods.

Silicone septa were prepared by in-place casting of the polymer.

Commercially available silicone O-rings were used for sealing the device at the appropriate connections.

In group 1, 15 mg of exenatide acetate was weighed out into reservoirs of the devices.

In group 2, 10 mg of exenatide and 10 mg of Diaion wk40L were weighed out into reservoirs of the devices.

The devices were sealed with the membranes in their titanium cap, and subsequently evacuated and packaged under vacuum.

The evacuated devices were sterilized by e-beam irradiation at 25 kGray at a temperature between −10 C and −20 C.

The devices were unpacked in a sterile biohood, and a vacuum was applied to the reservoir by evacuation through the membrane.

The devices were hydrated by inserting a hypodermic needle through the septum and injecting a sterile hydration buffer with 0.2M citrate buffer at pH 5.3 and 0.27% Polysorbate 20 (v/v) To aid in the hydration, vacuum was applied to the membrane side of the device during the hydration.

Devices were implanted dorsally in Sprague Dawley rats and retrieved at regular time intervals. The remaining inside solutions were collected for measurement of the pH and for determination of the exenatide purity by reverse phase HPLC.

Figure 3A:
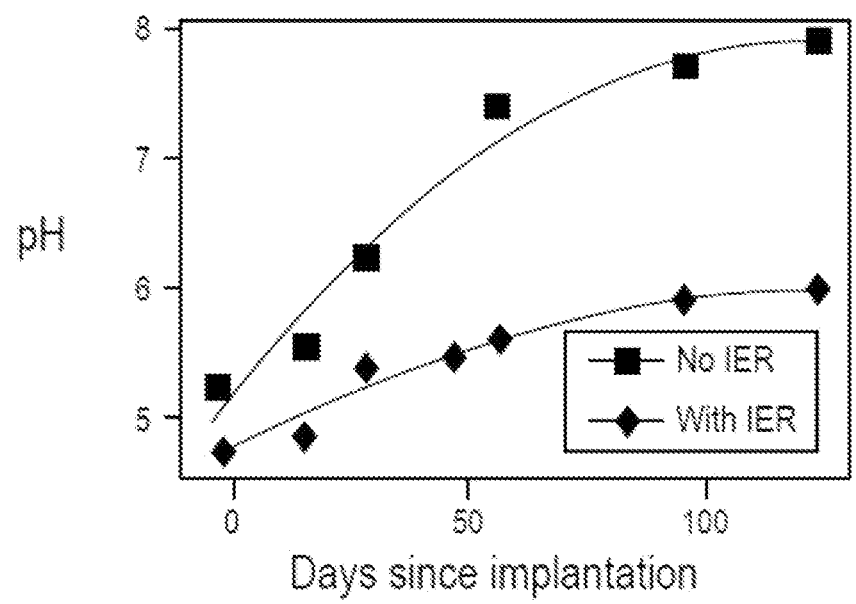
FIG. 3A represents the effect of a stabilizing agent of the disclosure on the pH of a therapeutic agent of the disclosure.
Figure 3B:
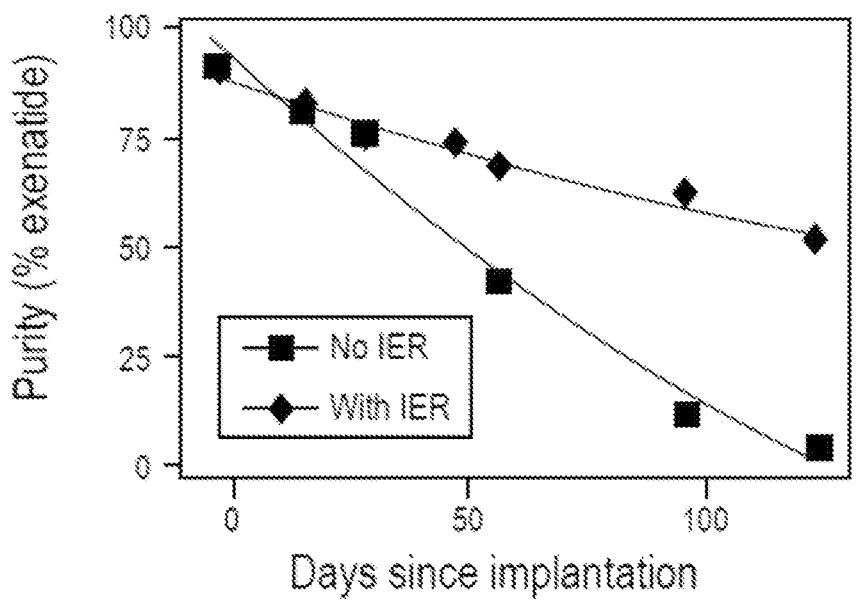
FIG. 3B represents the effect of a stabilizing agent of the disclosure on the purity of a therapeutic agent of the disclosure.

As can be seen in FIG. 3, the pH remained significantly lower in the devices with the stabilizing agent, and the purity remained significantly higher.

Example 18

Therapeutic agent: Exenatide acetate (Bachem Holding AG, Switzerland). (Exenatide Acetate, CAS Number: 914454-01-6).

Stabilizing agent: Diaion WK40L (Mitsubishi Chemical Corporation, Japan).

Membranes were developed based on the process as described in U.S. Pat. No. 9,814,867.

50 microliter polycarbonate capsules and titanium screw caps to attach the membrane to the capsule were prepared by commonly available machining methods.

Silicone septa were prepared by in-place casting of the polymer.

Commercially available silicone O-rings were used for sealing the device at the appropriate connections.

In group 1, 10 mg of exenatide and 10 mg of Diaion wk40L were weighed out into reservoirs of the devices.

In group 2, 15 mg of exenatide acetate was weighed out into reservoirs of the devices.

The devices were sealed with the membranes in their titanium cap.

The devices were hydrated by inserting a hypodermic needle through the septum and injecting sterile water for injection with 0.0011% Polysorbate 20 (v/v) into the reservoirs. To aid in the hydration, vacuum was applied to the membrane side of the device during the hydration.

The devices were submerged in 4 ml of sterile bis-tris buffer at pH 7.4 and 37 C to establish the effectiveness of the ion exchange resin to maintain pH and exenatide purity under in vitro conditions mimicking the in-vivo implantation conditions. At regular intervals devices were removed from the incubation buffer. The remaining inside solutions were collected for measurement of the pH and for determination of the exenatide purity by reverse phase HPLC.

Figure 4A:
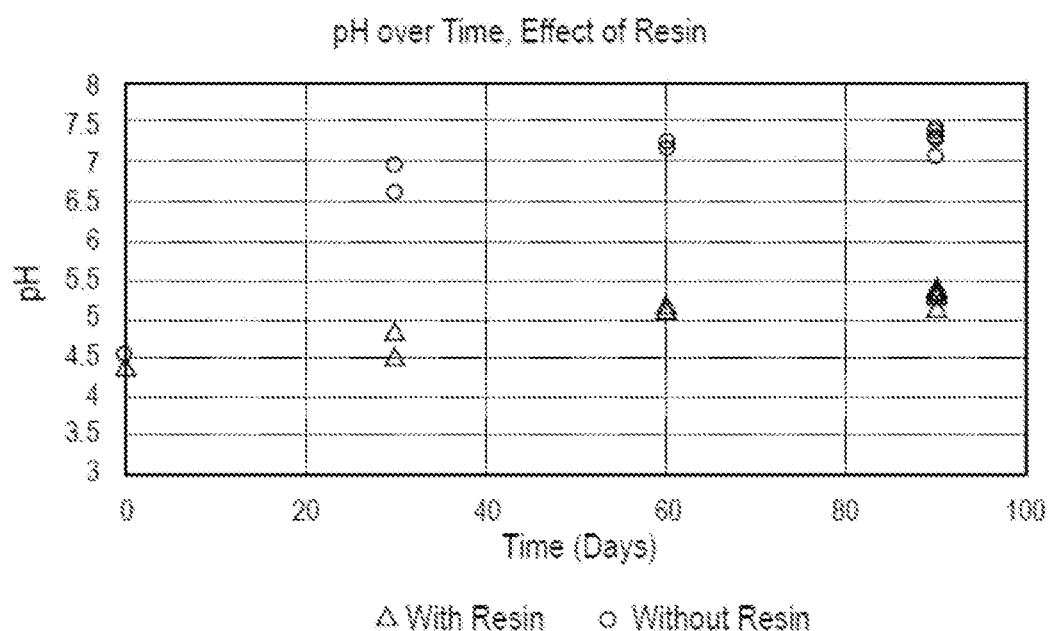
FIG. 4A shows the presence of an ion exchange resin maintained a lower pH over at least 3 months (90 Days).
Figure 4B:
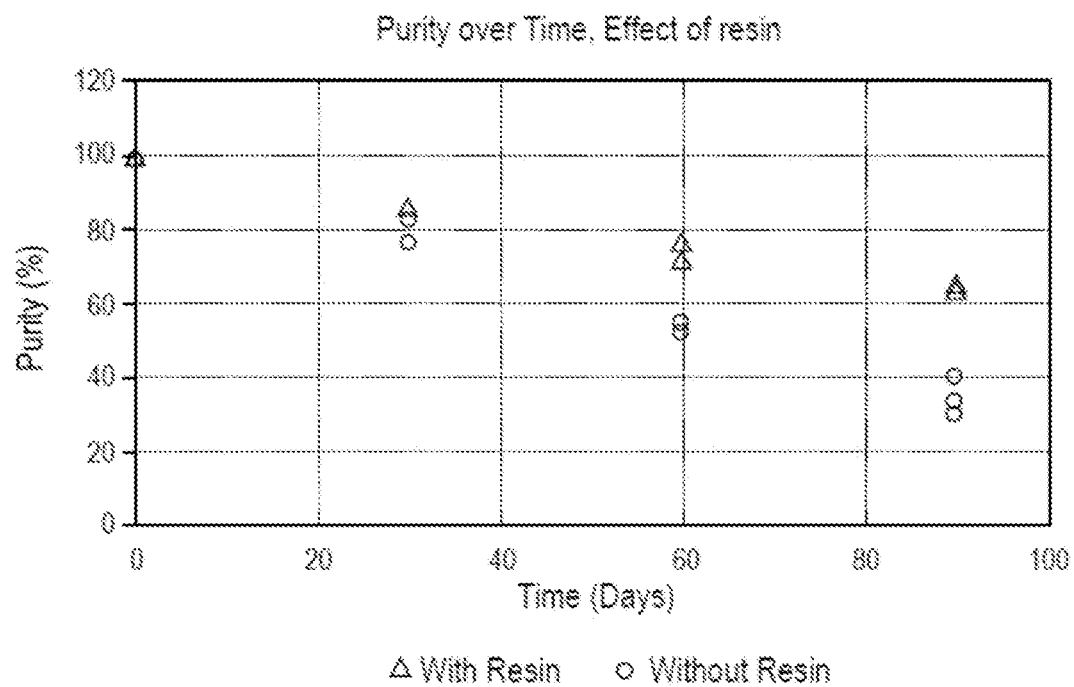
FIG. 4B shows the presence of an ion exchange resin maintained better purity of the exenatide over at least 3 months (90 Days).
Figure 5A:
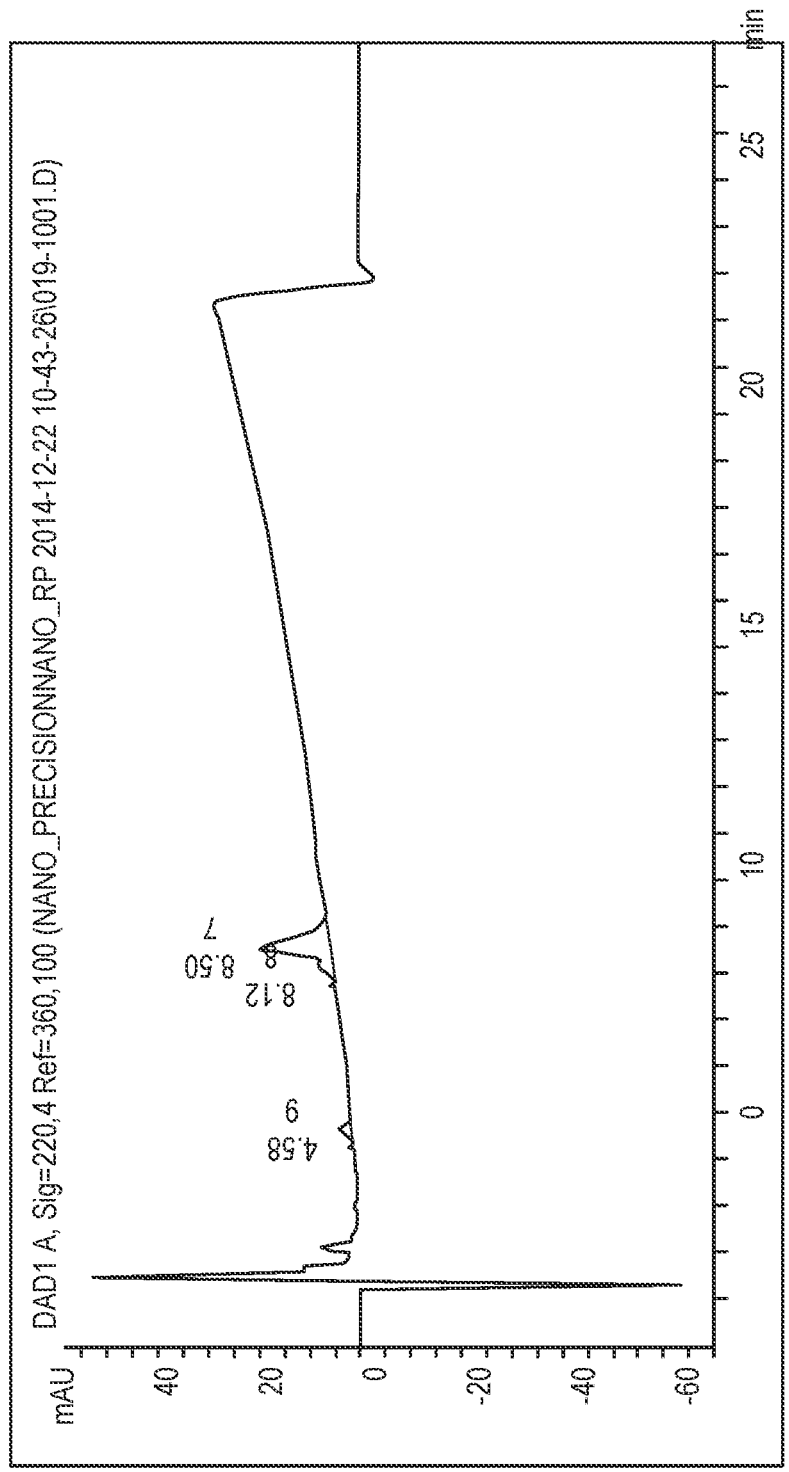
FIG. 5A shows the stability of exenatide in the compositions of the present disclosure without PAMAM-COOH.
Figure 5B:
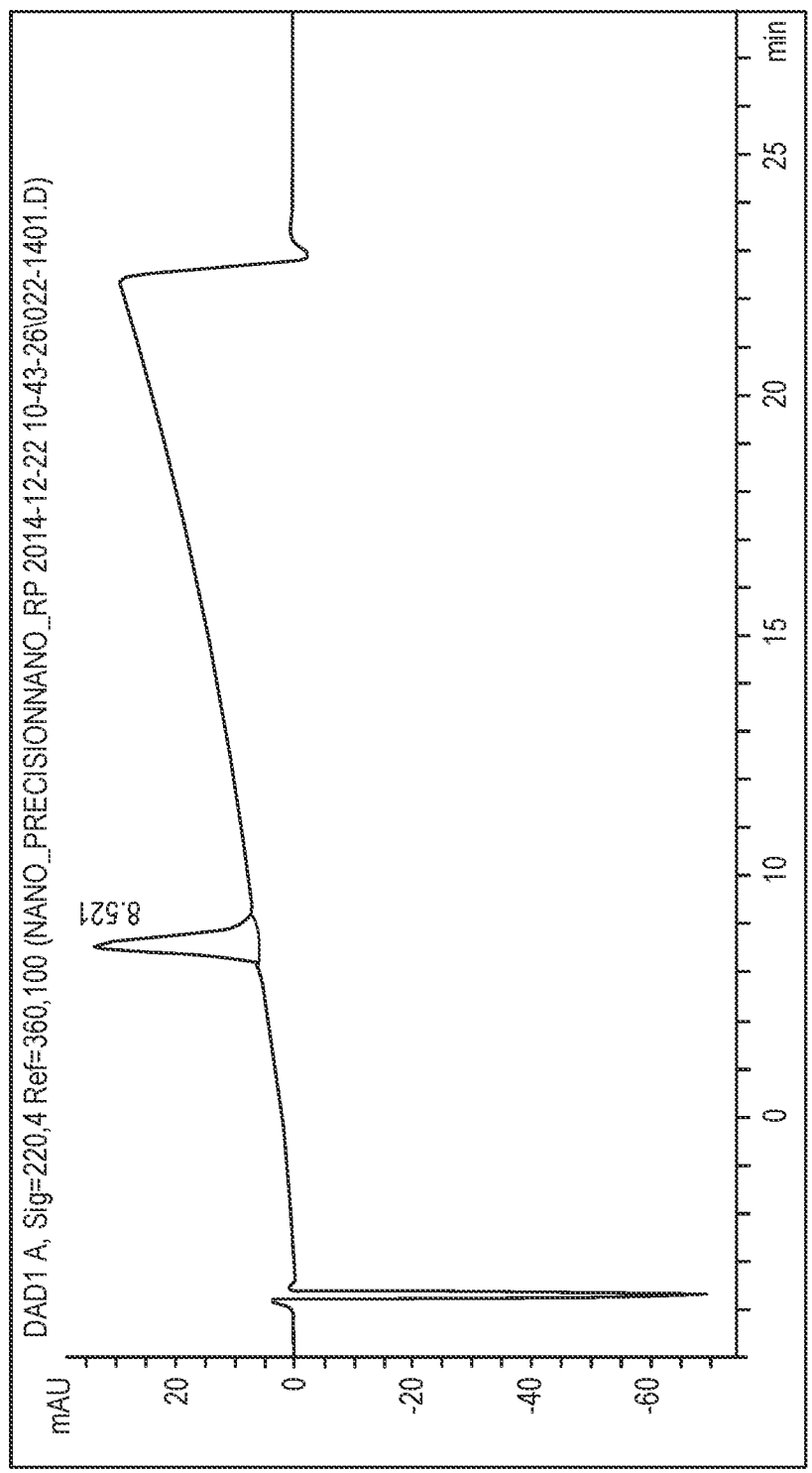
FIG. 5B shows the stability of exenatide in the compositions of the present disclosure with PAMAM-COOH.

As can be seen in FIGS. 4A and 4B, the presence of the ion exchange resin maintained a lower pH over at least 3 months, and significantly better purity of the exenatide.

Example 19

The Table below shows pH adjustment of an ion exchange resin (Purolite PPC104plus) with NaOH and NaCl.

| Sample ID | initial resin mass (g) | mL 1N NaOH | mL 2M NaCl | mL H$_2$O | Equilibrated pH | NaCl (mM) |
|---|---|---|---|---|---|---|
| 32 | 1.0 | 4.55 | 3.9 | 42 | 5.28 | 154.61 |
| 33 | 1.0 | 4.87 | 3.9 | 41 | 5.37 | 156.72 |
| 34 | 1.0 | 5.20 | 3.9 | 41 | 5.46 | 155.69 |
| 35 | 1.0 | 5.54 | 3.9 | 41 | 5.57 | 154.64 |
| 36 | 1.0 | 5.89 | 3.9 | 40 | 5.67 | 156.66 |

Purolite PPC104plus is a porous cross-linked polyacrylic acid in a spherical bead. The particle size ranges from 300-1600 μm.

All publications and patent applications cited in this specification are herein incorporated by reference as if each individual publication or patent application were specifically and individually indicated to be incorporated by reference. Although the foregoing disclosure has been described in some detail by way of illustration and example for purposes of clarity of understanding, it will be readily apparent to those of ordinary skill in the art in light of the teachings of this disclosure that certain changes and modifications may be made thereto without departing from the spirit or scope of the appended claims.

What is claimed is:

1. A method for stabilizing a pharmaceutical composition in a capsule configured to be implanted, the method comprising:
providing a pharmaceutical composition comprising a therapeutic agent, which therapeutic agent is a peptide, together with a polymeric stabilizing agent comprising a polymer having a plurality of stabilizing groups, wherein the polymer is a dendritic polymer or is a cross-linked polymer;
providing a capsule having a reservoir and a nanoporous membrane with a plurality of pores, wherein said pharmaceutical composition is disposed within the reservoir, the capsule configured for implantation; and
the polymeric stabilizing agent having molecular dimensions larger than the pore size of the nanoporous membrane, wherein the release of the polymeric stabilizing agent from the reservoir is substantially prevented; and wherein the nanoporous membrane is a diffusion pathway out of the reservoir for the therapeutic agent.

2. The method of claim 1, wherein the therapeutic agent is selected from the group consisting of beta-glucocerobrosidase, interferon alpha, interferon beta, agasidase alpha, agasidase beta, exenatide, nutropin/somatropin, factor VIII, fondaparinux, aldesleukinand, risperidone, forigerimod, NP fusion proteins, IL-12, a melanocyte stimulating hormone, and bapineuzumab.

3. The method of claim 1, wherein the therapeutic agent is selected from the group consisting of exenatide, octreotide and fluphenazine.

4. The method of claim 1, wherein the therapeutic agent comprises exenatide.

5. The method of claim 1, wherein the polymer is a dendritic polymer.

6. The method of claim 1, wherein the polymer is a poly(amidoamine) dendrimer having a plurality of end groups, wherein the plurality of end groups comprise at least one member selected from the group consisting of the acid groups, the base groups, alkyl, hydroxyalkyl, amidoethanol, amidoethylethanolamine, ethylenediamine, sodium carboxylate, succinamic acid, trimethoxysilyl, tris(hydroxymethyl)amidomethane, and 3-carbomethoxypyrrolidinone.

7. The method of claim 6, wherein the end groups of the poly(amidoamine) dendrimer comprise sodium carboxylate.

8. The method of claim 1, wherein each stabilizing group is independently selected from the group consisting of an acid group, a base group, an anti-oxidant, an anti-microbial, an anti-biotic, a protein clustering agent, and a protein declustering agent.

9. The method of claim 1, wherein each stabilizing group is independently selected from the group consisting of an acid group and a base group.

10. The method of claim 9, wherein the acid groups are selected from the group consisting of carboxylic acid, amino acid, thiol, and phenol.

11. The method of claim 9, wherein the acid groups are carboxylic acids.

12. The method of claim 9, wherein the base groups are selected from the group consisting of hydroxy, cyano, amine and carboxylate.

13. The method of claim 9, wherein the base groups are amines.

14. The method of claim 1, wherein the polymer has a molecular diameter of at least 3 nm.

15. The method of claim 1, wherein the polymer has a molecular diameter of at least 5 nm.

16. The method of claim 9, wherein the polymer is an acidic polymer selected from the group consisting of polyacrylic acid, polymethacrylic acid, polystyrene sulfonic acid, polyvinyl sulfonic acid, polyvinyl phosphonic acid and polystyrene phosphonic acid.

17. The method of claim 16, wherein the polymer is crossed-linked.

18. The method of claim 17, wherein the polymer is polyacrylic acid.

19. The method of claim 17, wherein the polymer is polymethacrylic acid.

20. The method of claim 1, wherein the capsule contains a second membrane.

* * * * *